US011422045B2

(12) United States Patent
Araromi et al.

(10) Patent No.: US 11,422,045 B2
(45) Date of Patent: Aug. 23, 2022

(54) ULTRA-SENSITIVE COMPLIANT STRAIN SENSORS

(71) Applicant: President and Fellows of Harvard College, Cambridge, MA (US)

(72) Inventors: Oluwaseun A. Araromi, Cambridge, MA (US); Conor J. Walsh, Cambridge, MA (US); Robert J. Wood, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 67 days.

(21) Appl. No.: 17/056,357

(22) PCT Filed: May 20, 2019

(86) PCT No.: PCT/US2019/033143
§ 371 (c)(1),
(2) Date: Nov. 17, 2020

(87) PCT Pub. No.: WO2019/226558
PCT Pub. Date: Nov. 28, 2019

(65) Prior Publication Data
US 2021/0215554 A1 Jul. 15, 2021

Related U.S. Application Data

(60) Provisional application No. 62/674,120, filed on May 21, 2018.

(51) Int. Cl.
*G01L 1/22* (2006.01)
*G01L 5/1627* (2020.01)
*G01B 7/16* (2006.01)

(52) U.S. Cl.
CPC .............. *G01L 1/2287* (2013.01); *G01B 7/18* (2013.01); *G01L 5/1627* (2020.01)

(58) Field of Classification Search
None
See application file for complete search history.

(56) References Cited

U.S. PATENT DOCUMENTS 9,351,900 B2 * 5/2016 Walsh ..................... A61F 2/68
2015/0173993 A1 * 6/2015 Walsh ................... B25J 9/0006
414/4

(Continued)

FOREIGN PATENT DOCUMENTS

WO WO 2013/146231 A1 10/2013
WO WO 2016/044251 A1 3/2016

OTHER PUBLICATIONS

International Search Report and Written Opinion for International Application No. PCT/US2019/033143, dated Oct. 9, 2019.

*Primary Examiner* — Brandi N Hopkins
*Assistant Examiner* — Nigel H Plumb
(74) *Attorney, Agent, or Firm* — Wolf, Greenfield & Sacks, P.C.

(57) ABSTRACT

A strain sensor comprising a conductive member having a plurality of elements arranged adjacent to one another, and a non-conductive and elastically deformable material encapsulating the conductive member, wherein, in an equilibrium state, compressive forces cause at least one of the plurality of elements to contact at least a portion of an adjacent element, and wherein, when a strain is applied, a resulting elastic deformation causes at least one of the plurality of elements to space apart from an adjacent element such that the contacted portion decreases or is eliminated. A multi-axis force sensor comprising a sensing array comprising at least two planar sensors arranged radially on a planar substrate in antagonistic pairs, and a compressible member positioned between the substrate and a central portion of the sensing array, the compressible member acting to displace (Continued)

the central portion of the sensing array away from the substrate.

37 Claims, 17 Drawing Sheets

(56) References Cited

U.S. PATENT DOCUMENTS

| | | | | |
|---|---|---|---|---|
| 2015/0321339 | A1* | 11/2015 | Asbeck | A61F 2/68 414/7 |
| 2016/0107309 | A1* | 4/2016 | Walsh | A61B 5/6831 248/550 |
| 2016/0220438 | A1 | 8/2016 | Walsh et al. | |
| 2016/0284231 | A1* | 9/2016 | Walsh | G09B 19/0038 |
| 2016/0346156 | A1* | 12/2016 | Walsh | A61H 3/008 |
| 2017/0027735 | A1* | 2/2017 | Walsh | A61F 5/0123 |
| 2017/0176167 | A1* | 6/2017 | Keller | G01L 1/225 |
| 2017/0202724 | A1* | 7/2017 | De Rossi | A61H 3/00 |

* cited by examiner

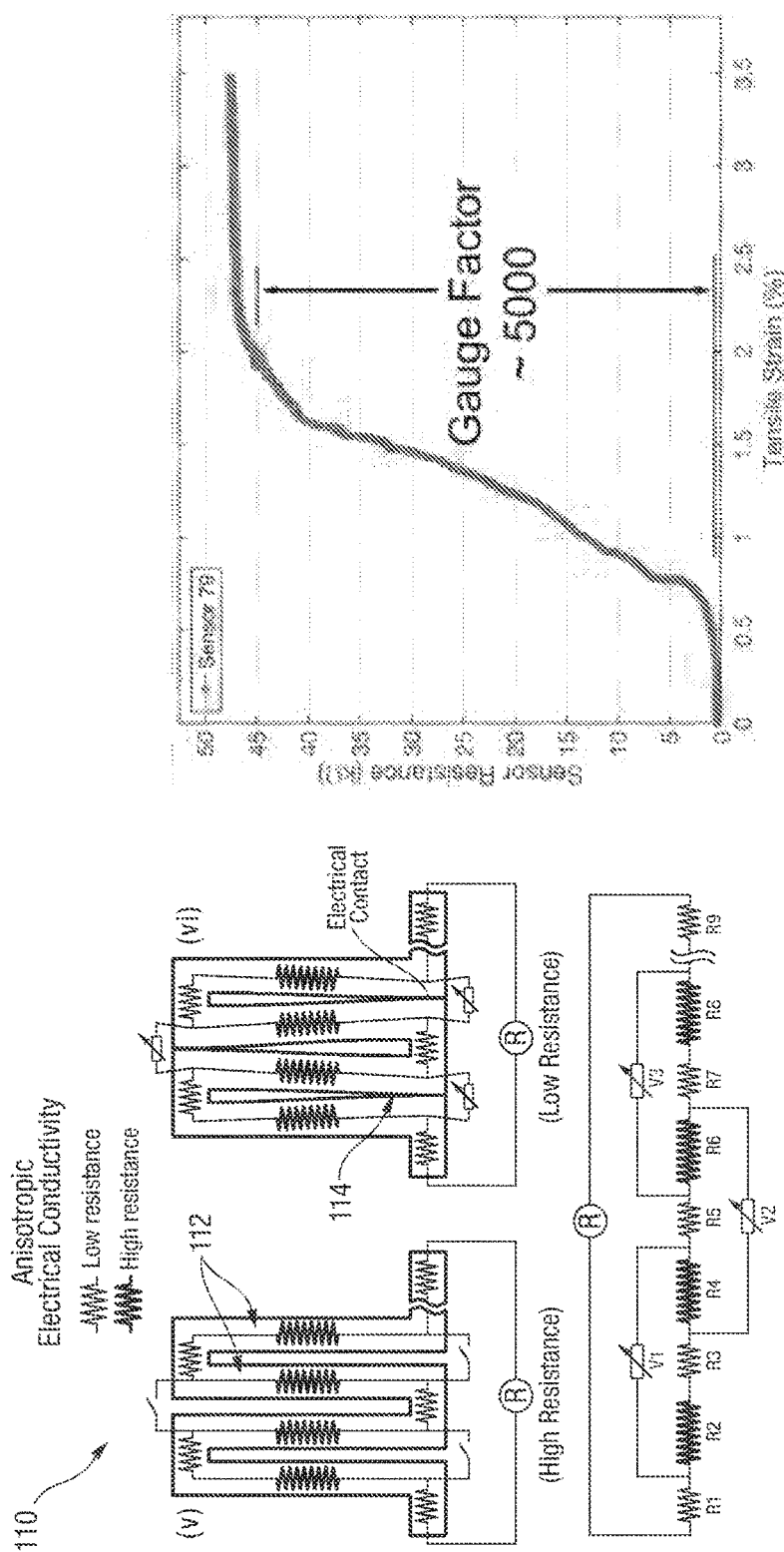

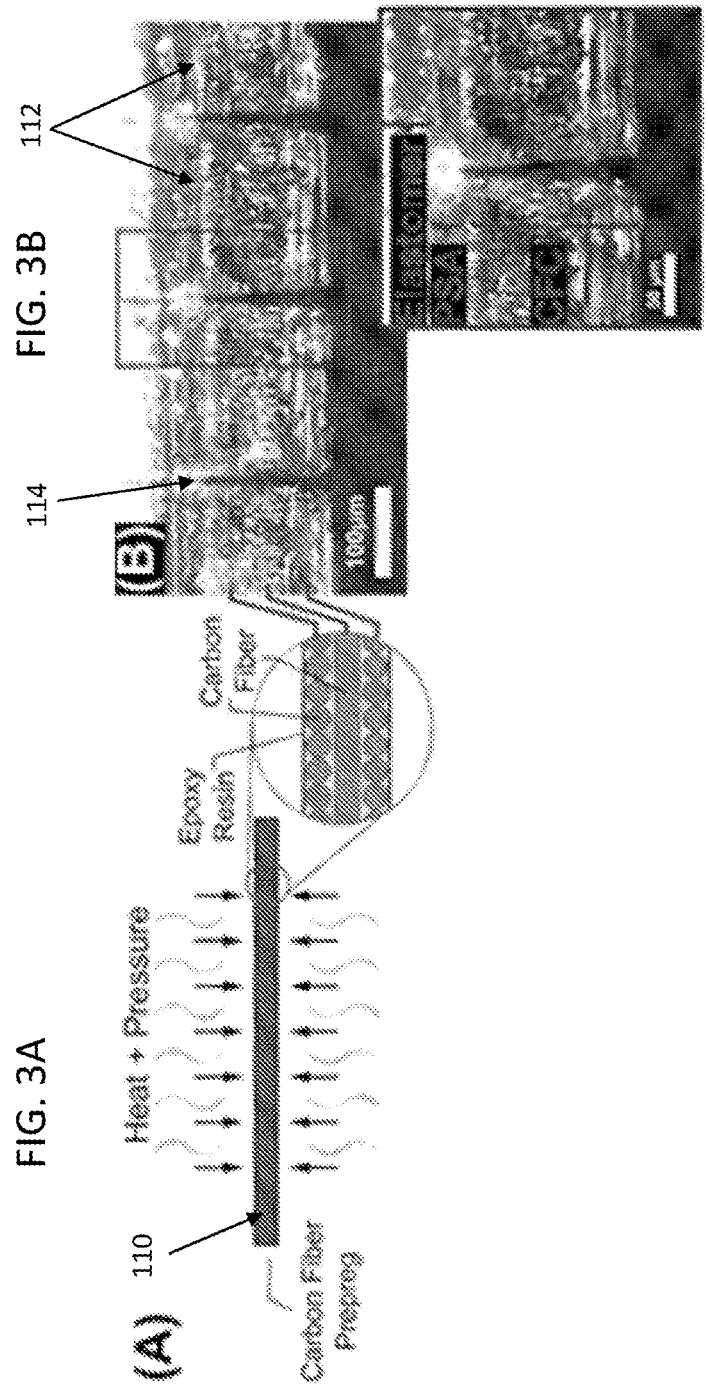

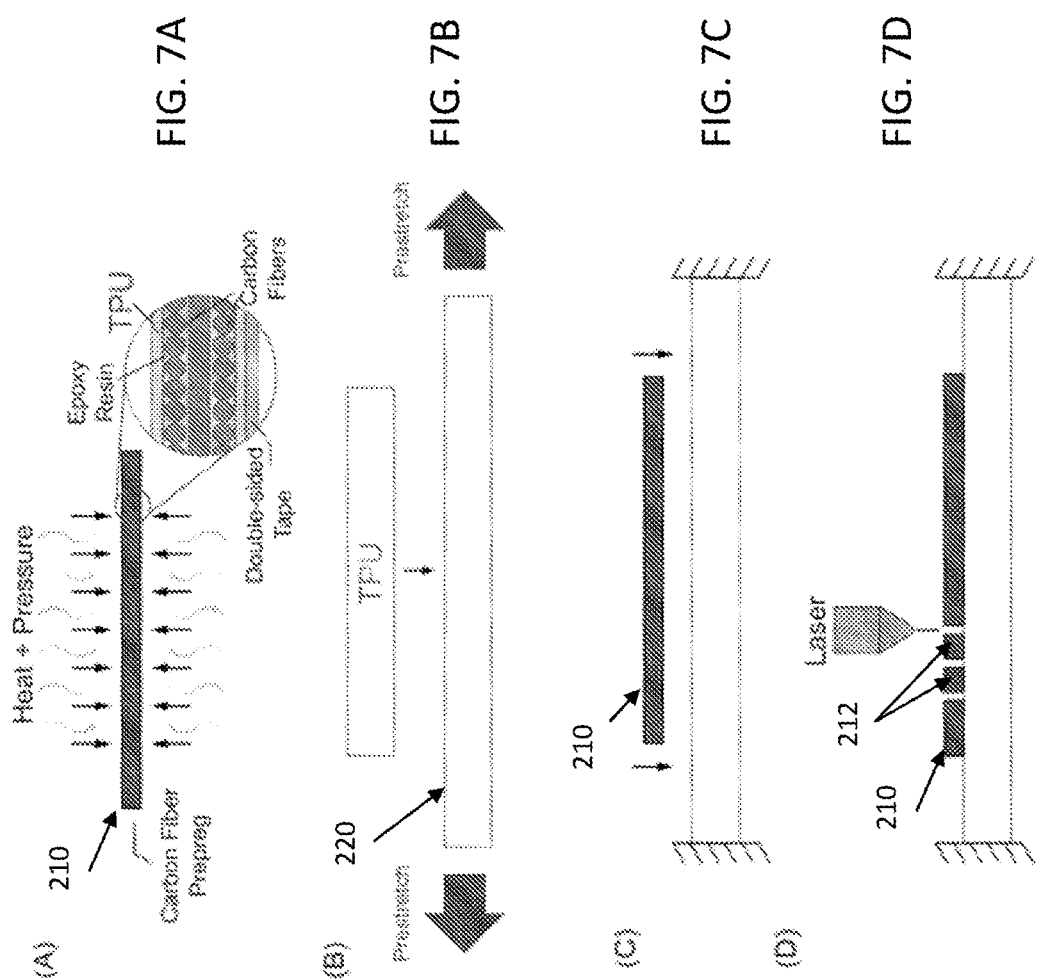

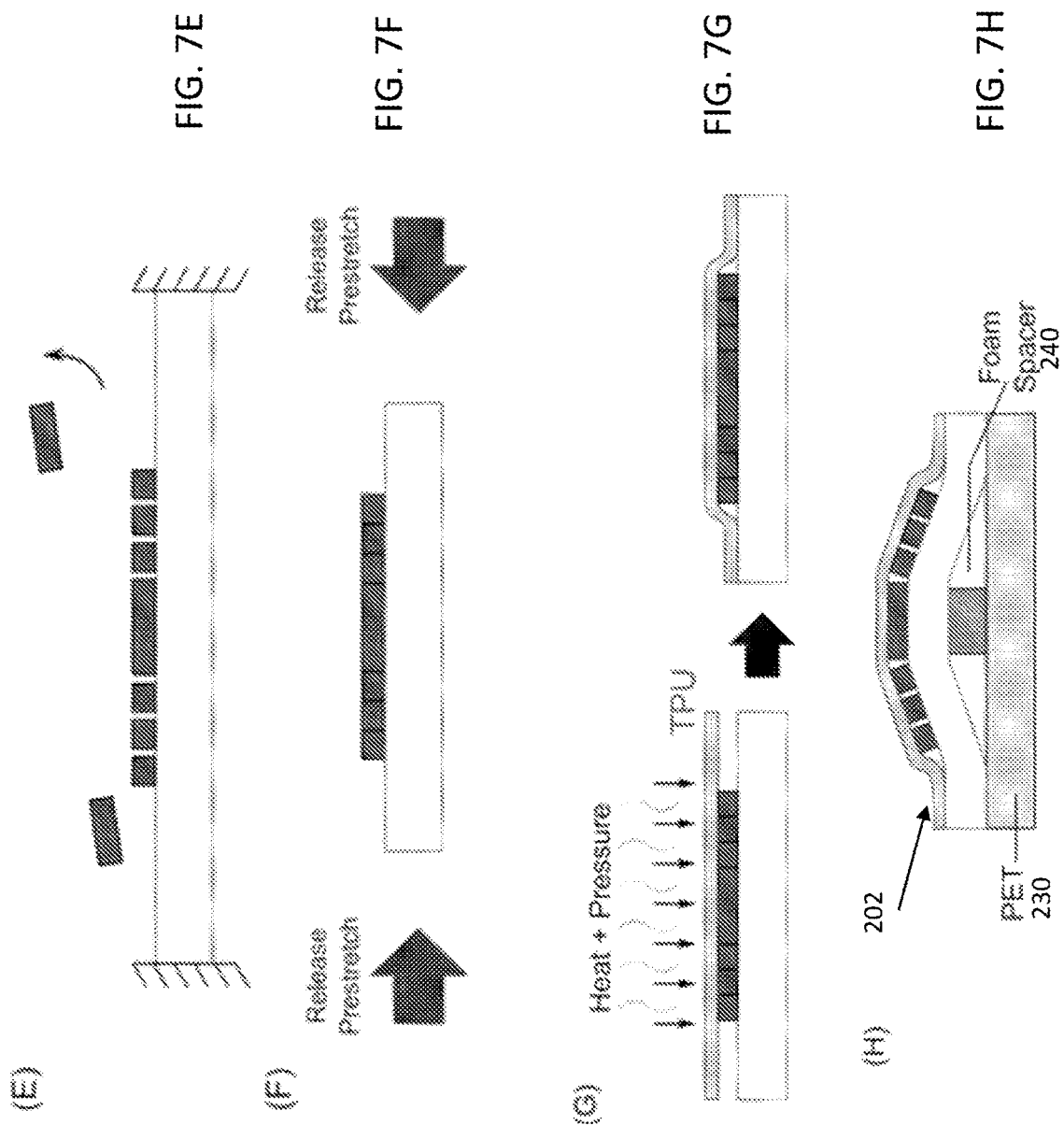

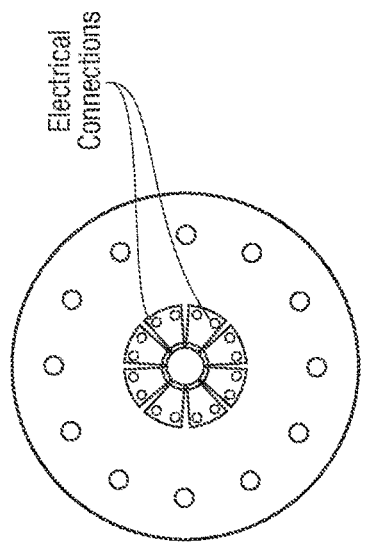
FIG. 8H
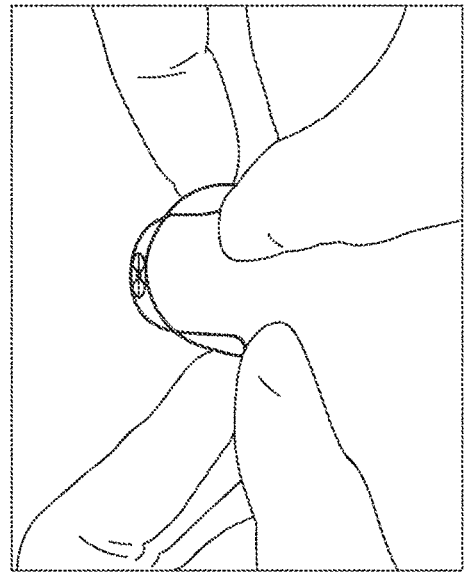
FIG. 8I
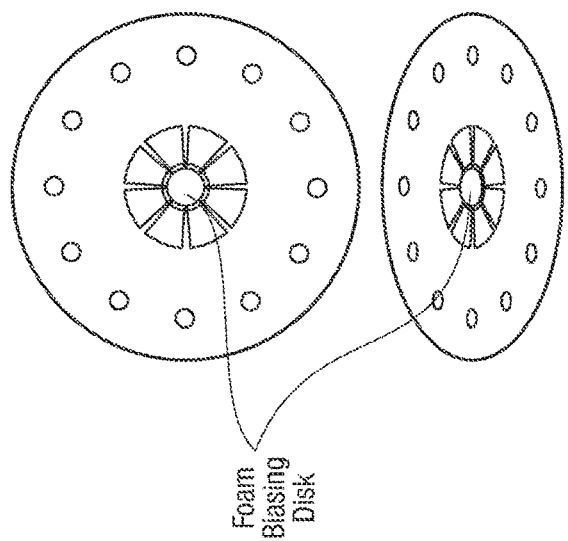
FIG. 8G
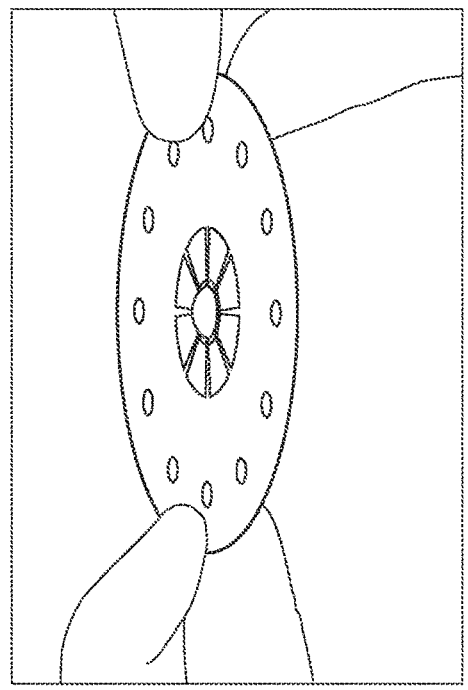

ULTRA-SENSITIVE COMPLIANT STRAIN SENSORS

CROSS-REFERENCE TO RELATED APPLICATIONS

The application is a national stage filing under 35 U.S.C. § 371 of international application number PCT/US2019/033143, filed May 20, 2019, which claims the benefit of and priority under 35 U.S.C. § 119(e) to U.S. Provisional Application No. 62/674,120, filed May 21, 2018, the entire contents of each of which are hereby incorporated by reference for all purposes.

STATEMENT REGARDING FEDERALLY SPONSORED RESEARCH OR DEVELOPMENT

This invention was made with government support under contract numbers W911NF-14-C-0051 and W911NF-13-1-0311, awarded by the U.S. Army Research Office. The government has certain rights in the invention.

BACKGROUND

The development of soft, compliant force sensors is greatly sought after in areas such as soft robotics and prosthetics. Nevertheless, solutions for measuring forces in multiple axes, while being mechanically compliant, have been few and far between.

Several soft or compliant sensor concepts have been proposed in the literature for measuring linear strains (e.g. for joint angle measurement) [1], [2], [3], and those optimized to measure normal pressure [4], [5], [6]. However, relatively few approaches have been developed for measuring forces in multiple degrees of freedom (DOFs).

Measurements of forces tangential to a surface (i.e. shear) can be useful for establishing the relative motion between a wearable device or a robotic prosthetic and the skin of a user, and could help to determine pressure points or areas of excessive friction. Vogt et al. developed a soft, multi-axis force sensor concept based on the deformation of micro channels in an elastomer composite filled with liquid metal [7].

Though very effective, the sensor had a thickness of several millimeters, making it less ideal for wearable applications. The compliant shear sensor design presented by Toyama et al. based on the relative translation of two planar electrodes separated by ionic liquid and has a low form factor [8]. However, the use of a liquid may result in large changes in volume or conductivity with temperature, and may present problems regarding mechanical resilience and long survivability.

SUMMARY

Systems and methods for ultra-sensitive compliant strain sensors are disclosed herein. In an embodiment, a strain sensor includes an electrically conductive member having a plurality of elements arranged adjacent to one another; and an electrically non-conductive and elastically deformable material encapsulating the electrically conductive member, wherein, when the sensor is in an equilibrium state, compressive forces stored in the electrically non-conductive and elastically deformable material cause at least one of the plurality of elements to contact at least a portion of an adjacent element of the electrically conductive member, thereby forming an electrically conductive pathway between the adjacent elements through the contacted portion, and wherein, when a strain is applied to the sensor, a resulting elastic deformation of the electrically non-conductive and elastically deformable material causes at least one of the plurality of elements to space apart from an adjacent element such that the contacted portion decreases or is eliminated, thereby reducing or eliminating the electrically conductive pathway between the adjacent elements and increasing a resistance of the electrically conductive member (for example, the total electrical resistance of the electrically conductive member).

In an embodiment, a multi-axis force sensor includes a planar substrate; a sensing array comprising at least two planar sensors arranged radially on the substrate in antagonistic pairs, each planar sensor comprising: an electrically conductive member extending radially and having a plurality of elements arranged adjacent to one another, and an electrically non-conductive and elastically deformable material encapsulating the electrically conductive member and applying an in-plane compressive force on the electrically conductive member; and a compressible member positioned between the substrate and a central portion of the sensing array, the compressible member acting to displace the central portion of the sensing array away from the substrate.

In an embodiment, a method for manufacturing a sensor includes encapsulating an electrically conductive member within an electrically non-conductive and elastically deformable material, the electrically conductive member comprising a plurality of elements arranged adjacent to one another and spaced apart from one another; and contracting or allowing the electrically non-conductive and elastically deformable material to contract in-plane, thereby causing each of the plurality of elements to contact at least a portion of an adjacent element of the electrically conductive member.

BRIEF DESCRIPTION OF THE DRAWINGS

FIG. 2C shows an electric circuit representation of the conductive meander in the electric circuit pre (left) and post prestretch (right) release with the circuit representation for the post release state (bottom). Prior to releasing prestretch, the traces of the meander do not touch and the overall electrical resistance is determined simply by the sum of the series resistance of the traces. Once the prestretch is released the overall electrical conductivity is reduced as adjacent traces touch and create parallel resistance paths. With sufficient contact pressure, the touching traces create an electrical short-circuit effectively reducing the conduction path-length and hence the overall sensor resistance.

FIG. 2D shows an example of a sensor response from a fabricated device. Gauge factor or approximately 5,000 demonstrated in the region 0-2% strain.

FIG. 3A shows a schematic of carbon fiber composite lay-up manufacture.

FIG. 3B shows cross-section images of laser machined traces prior to prestretch release showing the three layer CFC lay-up, PSA and elastomer. Inset shows zoom of central two traces, slanted trace edge is a result of the laser machining step.

FIG. 7A shows a carbon fiber composite (CFC) lay-up manufacture.

FIG. 7B shows a 300 μm thick TPU film, prestretched biaxially in-plane.

FIG. 7C shows the CFC film adhered to the TPU using double-sided tape.

FIG. 7D shows the CFC lay-up micromachined using a laser.

FIG. 7E shows excess CFC material removed by peeling.

FIG. 7F shows the prestretch in the TPU relaxed, causing the meanders of the micro-structured CFC to come into contact with each other (short circuiting the electrical conduction path).

FIG. 7G shows the CFC meanders encapsulated by a 30 μm TPU film by heat bonding.

FIG. 7H shows a biasing spacer placed underneath the encapsulated traces and the sensor bonded to a PET substrate.

FIG. 8G shows the foam disk adhered to the sensor underside.

FIG. 8H shows the electrical connection made using metal pins inserted through CFC and TPU layers.

FIG. 8I shows a demonstration of sensor compliance and low form factor.

DETAILED DESCRIPTION

Soft, compliant force sensors are greatly sought after in the realms of wearable electronics, wearable robotics, soft robotics, dexterous grippers, and prosthetics. Moreover, mechanical robustness and resilience are also desired in order to increase device longevity, especially in applications where the sensor is likely to be subjected to frequent bending (e.g. wearable applications).

Uniaxial Strain Sensor 100

Figure 1:
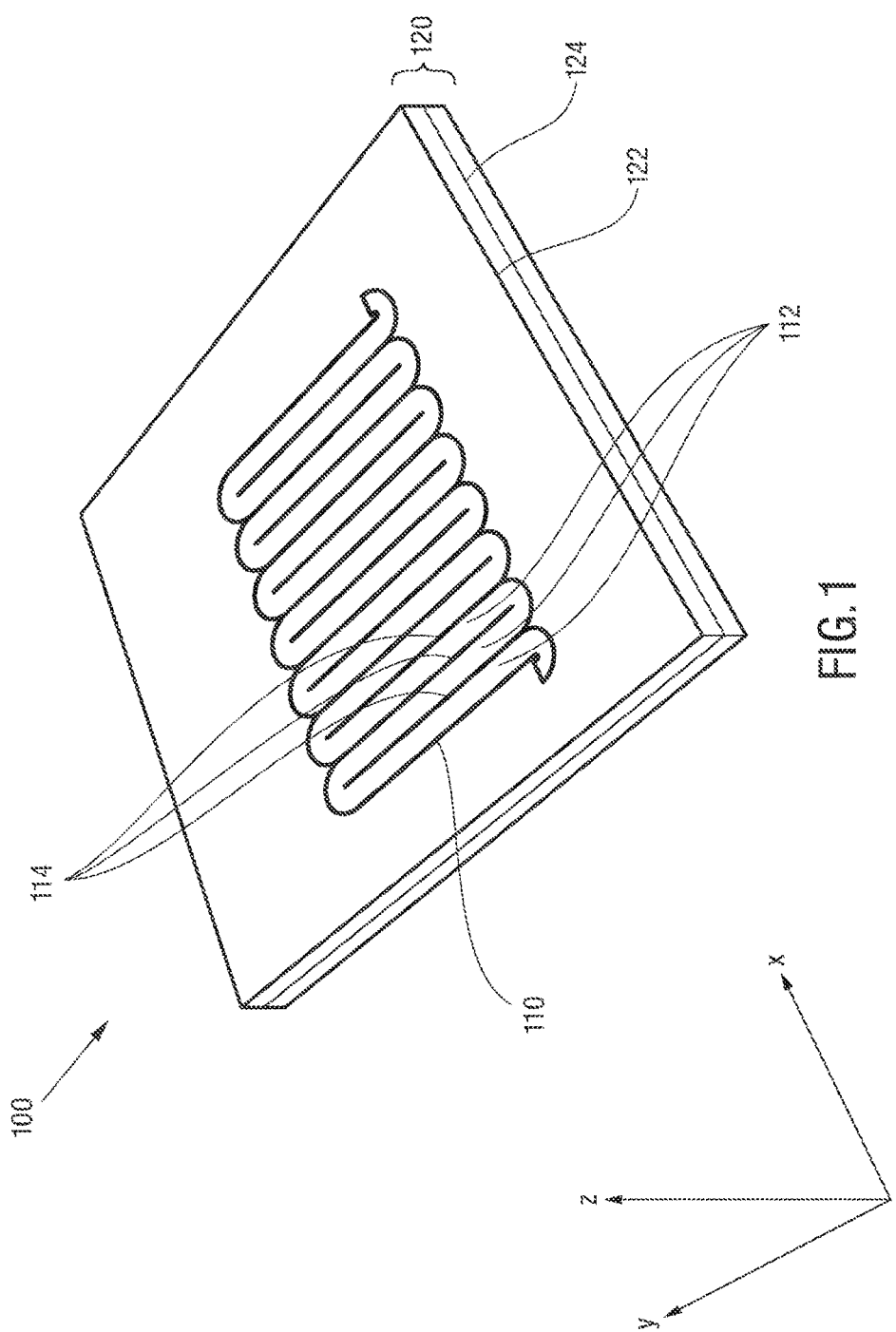
FIG. 1 shows a compliant, low-profile, low-strain strain sensor based on the strain-mediated variation in conduction path length in anisotropically conductive microstructures.

Referring to FIG. 1, we present a compliant, low-profile, low-strain strain sensor 100 (or strain gauge) based on the strain-mediated variation in conduction path length in anisotropically conductive microstructures (or smaller, such as nanostructures). These strain sensors 100 transduce small strains, typically less than 3%, as large changes in electrical resistance, and are ideal for measuring forces in materials integrated mechanically in parallel with them.

Strain sensor 100, in various embodiments, may generally comprise an electrically conductive member 110 having a plurality of elements 112 arranged adjacent to one another, as well as an electrically non-conductive and elastically deformable material 120 encapsulating the electrically conductive member 110. Generally speaking, when strain sensor 100 is in an equilibrium state, compressive forces stored in electrically non-conductive and elastically deformable material 120 (hereinafter referred to as "encapsulation material 120") may cause at least one of the plurality of elements 112 to contact at least a portion of an adjacent element 112 of the electrically conductive member 100, thereby forming an electrically conductive pathway between the adjacent elements through the contacted portion 114. When a strain is applied to the sensor 100, a resulting elastic deformation of encapsulation 120 may cause at least one of the plurality of elements 112 to space apart from an adjacent element 112 such that the contacted portion 114 decreases or is eliminated, thereby reducing or eliminating the electrically conductive pathway between the adjacent elements 112 and increasing a resistance of the electrically conductive member 110. The resulting change in resistance of electrically conducive member 110, in various embodiments, may be measured and correlated with a corresponding magnitude of the applied force (e.g., strain), as later described in more detail. In an embodiment, strain sensor 100 may be substantially planar in shape.

Electrically Conductive Member 110

Still referring to FIG. 1, electrically conductive member 110, in various embodiments, may include any electrically conductive material having high mechanical strength, high flexibility, and good elastic recovery. For example, in a representative embodiment, electrically conductive member 110 may be formed of a carbon fiber composite (CFC) material. Referring to FIG. 3A, the CFC material forming electrically conductive member 110, in an embodiment, may include aligned carbon fibers set in an epoxy matrix. The aligned carbon fibers, in an embodiment, may be approximately 3 μm in diameter. The CFC lay-up, in various embodiments, may made by stacking three (or more) layers of carbon fiber sheets pre-impregnated with an epoxy resin (e.g., Toho Tenax, by Teijin). The three CFC layers may be laid orthogonal to each other, as depicted in FIG. 3A, resulting in an increased electrical conductivity in the fiber direction of the outer layers. As configured, such a construction may provide the CFC material with anisotropic properties, as later described in more detail. In another embodiment, electrically conductive member 110 may be formed of a super elastic shape-memory alloy. In yet another embodiment, electrically conductive member 110 may be formed of a super elastic alloy. One of ordinary skill in the art will recognize other suitable having similar properties that may be suitable for use in forming electrically conductive member 110 in accordance with the teachings of the present disclosure.

Figure 3D:
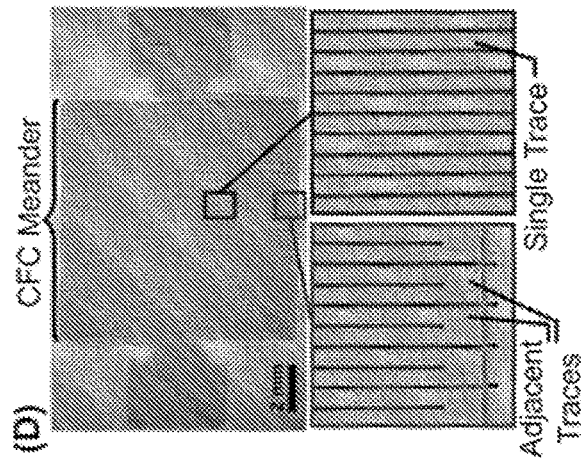
FIG. 3D shows images from a scanning electron microscope of fabricated CFC meander.
Figure 3C:
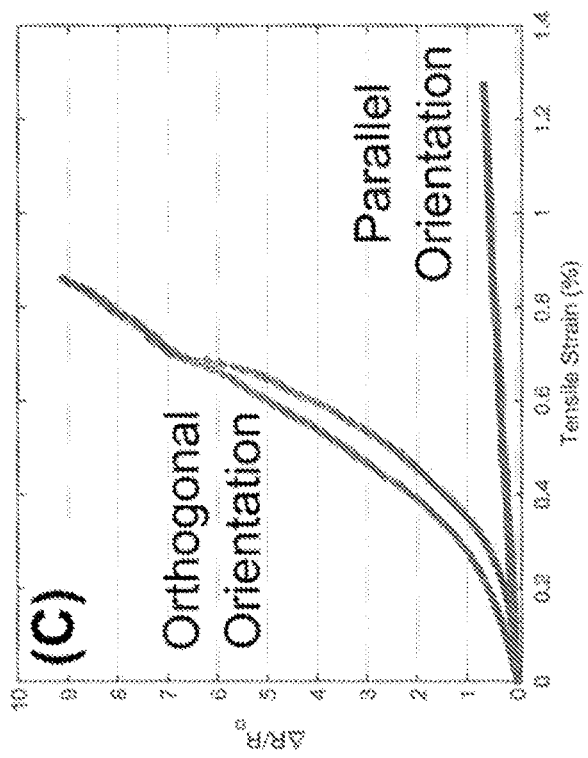
FIG. 3C shows a graph demonstrating the effect of rotating the high conductivity orientation 90 degrees in-plane. The sensor which has the high conductivity orientation aligned "Orthogonal"(lateral) to the trace length-wise dimension rather than parallel is much more sensitive.

As shown in FIG. 3C, electrical conductivity anisotropy may have a significant affect on the performance of sensor 100. For example, if the anisotropy is oriented such that the high conduction dimension (e.g., the outer layers of the aforementioned CFC layup) extends lengthwise along elements 112, as shown in FIG. 3B, then the sensitivity of sensor 100 may be significantly decreased. Conversely, if the anisotropy is oriented such that the high conduction dimension (e.g., the outer layers of the aforementioned CFC layup) extends laterally across elements 112, then the sensitivity of sensor 100 may significantly increase. Without wishing to be bound by theory, it is thought that the contacted portion 114 between adjacent elements 112 forms a low resistance pathway between the elements 112, essentially allowing current to jump (or flow) across elements 112 rather than having to follow the full length of each element 112 before flowing into the adjacent element 112, much like opening a gate(s). This, in turn, may reduce the overall resistance of electrically conductive member 110. When a strain is applied, the sensor 110 elongates, causing contacted portions 114 to shrink or disappear as elements 112 space apart, thereby increasing the overall resistance of electrically conductive member 110. Thus, by orienting the high conduction dimension (e.g., the outer layers of the aforementioned CFC layup) to extend lengthwise along elements 112 (parallel with the Y-direction shown in FIG. 1), the current will tend to follow the length of the elements 112 rather than jumping across via the difference in resistance between when elements 112 are spaced apart and the equilibrium state (where adjacent elements 112 are in contact) is less, thereby changing the resistance of strain sensor to a lesser extent (thus, decreasing sensitivity) than if the high conduction dimension were oriented laterally across elements 112 (parallel with the X-direction shown in FIG. 1).

Electrically conductive member 110, in various embodiments, may be a continuous structure. For example, in the embodiment shown in FIG. 1, electrically conductive member 110 may be a meander having a serpentine-like shape that places sections of the conductive member 110 adjacent to one another, thereby defining elements 112. The meander, in an embodiment, may be formed by doubling an elongated conductive filament back on itself multiple times, while in another embodiment, may be formed by cutting out the profile of the meander from a planar piece of material, such as via a laser cutting process later described in more detail. In such embodiments, each elements 112 may be connected to an adjacent element 112, such as by the turns at the top and bottom of the serpentine meander shown in FIG. 1. However, in another embodiment, electrically conductive member 110 may simply include a plurality of individual elements 112 that are arranged adjacent to one another, but not physically connected to one another. In such an embodiment, some or all of these elements 112 may be brought into contact with adjacent elements 112 by releasing the pre-stretch of encapsulation 120 to form a contacted portion 114 therebetween. Without wishing to be bound by theory, current may flow through these contacted portions and thereby across electrically conductive member 110, and a resistance would vary based on the size of the contacted portions.

Adjacent elements 112 of electrically conductive member 110, in some embodiments, may be arranged parallel to one another as shown in FIG. 2C, while in other embodiments, adjacent elements 112 may be oriented slightly askew from one another as shown in FIG. 3B. For example, in an embodiment, adjacent elements may be angled away from one another by up to 30 degrees. One of ordinary skill in the art will recognize that elements 112 may be presented in any orientation suitable for allowing adjacent elements 112 to come into contact with one another in an equilibrium state in the presence of compressive forces applied by encapsulation 120.

The material, dimensions, and geometry of electrically conductive member 110, in various embodiments, may define the initial electrical resistance and also the mechanical stiffness of elements 112. For example, thinner elements 112, for a given over all area of electrically conductive member 110, may result in a higher initial resistance and also a reduced mechanical stiffness. Hence, a comparatively lower prestretch in encapsulation 120 may be required to produce a given element deflection for a given spacing of thinner elements 112. Conversely, a comparatively higher prestretch in encapsulation 120 may be required to produce a given element deflection for a given spacing of thicker elements 112. Likewise, the spacing between elements 112 may also contribute to the how much deflection is required for adjacent elements 112 to make electrical contact. Generally speaking, the greater the spacing between adjacent elements 112, the greater the amount of prestretch required to bring adjacent elements 112 into electrical contact (via the resulting contacted portion 114), all other things equal.

Encapsulation 120

Still referring to FIG. 1, encapsulation 120, in various embodiments, may include any material that is substantially non-conductive and has elastic properties (i.e., naturally restores from elongated to shortened). For example, representative materials having these properties include, without limitation, elastomers (e.g. silicone, acrylic, natural rubber), thermoplastic elastomers (e.g. thermoplastic polyurethane), gels (e.g. hydro-gels, silicone gels), textiles (e.g. knits, wovens, non-wovens or synthetics). One of ordinary skill in the art will recognize other suitable having similar properties that may be suitable for use in forming encapsulation 120 in accordance with the teachings of the present disclosure.

As shown in FIG. 1, in an embodiment, encapsulation 120 may include a first layer 122 and a second layer 124 of material bonded together to form an encapsulation around electrically conductive member 120 as later described in more detail. Generally speaking, in various embodiments, regardless of the particular construction, encapsulation 120 may be thought of an elastic substrate on or within which electrically conductive member 120 is situated and compressed in an equilibrium state. As later described in more detail, during the fabrication of sensor 100, encapsulation 120 may be prestretched about electrically conductive member 110 so as to store compressive forces for bringing elements 112 into contact with one another.

The prestretch in the encapsulation material 120, for a given encapsulation 120 geometry, may govern the amount of stored elastic energy, and hence amount of shear stress transmitted to the elements 112, and therefore the resistance range of sensor 100. In this work, prestretches less than 5% were used. Excessive prestretch results in a saturation zone at the beginning of the sensor response. This is because at a certain point, the electrical resistance between adjacent traces at equilibrium approaches a minimum as the contact area reaches a maximum. Accordingly, in an embodiment, prestretch may not exceed about 50%. Further increasing the prestretch beyond this point brings proportionally less of a change in the contact resistance, reducing the sensor sensitivity in the initial portion of its response and the overall sensor linearity.

Compressive strains can also be induced by using materials in encapsulation 120 which experience thermal shrinkage when exposed to high temperatures. For example, materials with suitable properties may include themoplastic polyurethane (TPU) and polyester TPU. In this case, mechanical prestretch may not be required; electrically conductive member 100 may be bonded to encapsulation 120 and subsequently exposed to heat to induce thermal shrinking and causing elements 112 to come into contact. This would have the same effect as releasing mechanical prestretch from a prestretched material. In certain applications this may be an easier method of inducing compressive strains.

In various embodiments, an adhesive (not shown) may be used to bond electrically conductive member 110 to encapsulation 120, and/or to bond layers of encapsulation 120 to one another (e.g., layers 122, 124). In an embodiment, the adhesive may be a pressure sensitive adhesive (PSA) that forms a bond when pressure is applied to couple the adhesive with electrically conductive member 110 and/or to layers 122, 124. The adhesive, in various embodiments, may have a low Young's modulus and is able to shear sufficiently to permit adjacent elements 112 to come into contact with each other. In some embodiments, the adhesion strength of the adhesive in contact with elements 112 is low in the shear direction, so as to allow more sliding of the adjacent elements, permitting them to come into contact more easily. In some embodiments, the adhesive may be patterned so that the adhesive in not in contact with adjacent elements 112 at their edges, so as to more easily allow adjacent elements to come into contact.

Fabrication

Figure 2B:
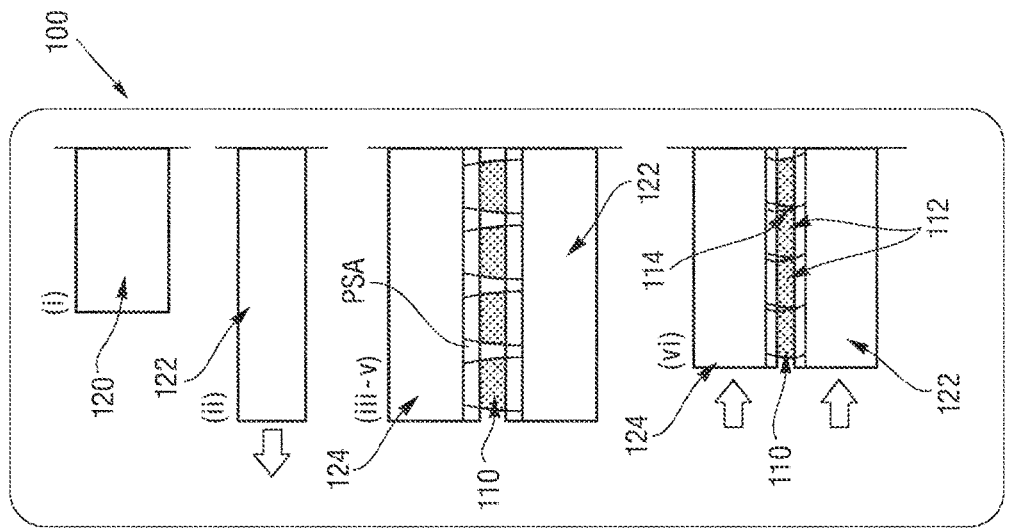
FIG. 2B shows a cross-sectional view of the various steps in the sensor fabrication process mentioned in connection with FIG. 2A (cross section relative to the orientation shown in FIG. 2A(i): (i) Elastomer in reference state. Lines depict shear stress variations along the thickness of the elastomer layer. (ii) Elastomer prestretching, showing reduced thickness as a result of material incompressibility (volume of material assumed to be a constant). (iii)-(iv) Conductive meanders post bonding step, sandwiched between two prestretched elastomers. (iv) The prestretch in the elastomer layers is released. Shear stresses are transmitted to the conductive meander through the PSA layer. Shearing in the adhesive layer allows adjacent traces to come into electrical contact with each other, reducing the overall electrical resistance of the meander.
Figure 2A:
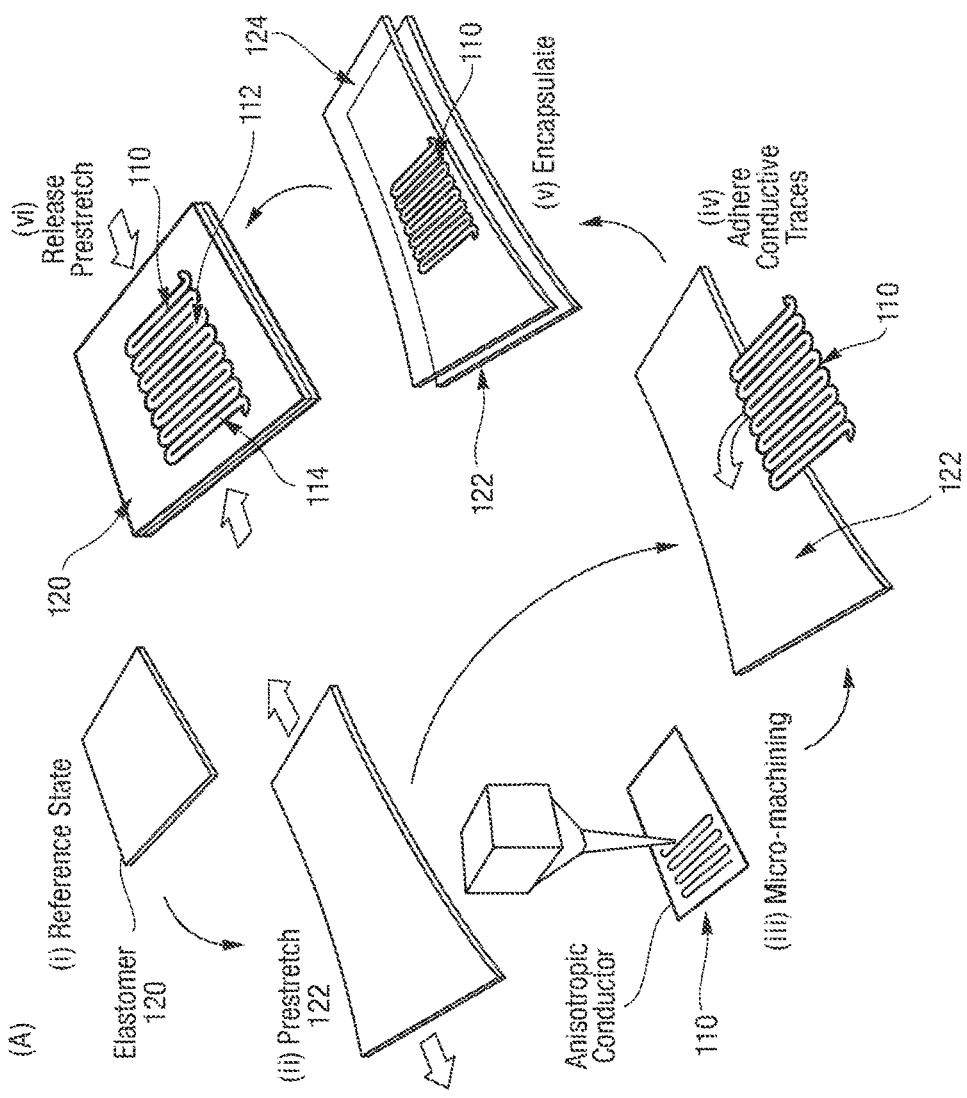
FIG. 2A shows a chart of the sensor fabrication process: (i) A thin elastomer substrate in the reference (un-prestretched) state. (ii) Elastomer substrate is prestretched. (iii) A meander pattern is laser micro-machined out an thin, anisotropically conductive material. The meander is bonded to the prestretched substrate using a pressure sensitive adhesive (PSA), as also shown in FIG. 2B. A second prestretched elastomer layer is bonded on top of the meander. (vi) The prestretch in the elastomer layers is released imposing a compressive load on the conductive meander via shear stresses transmitted through the adhesive.

FIG. 2A and FIG. 2B illustrate a representative approach for fabricating an embodiment of sensor 100.

Figure 3E:
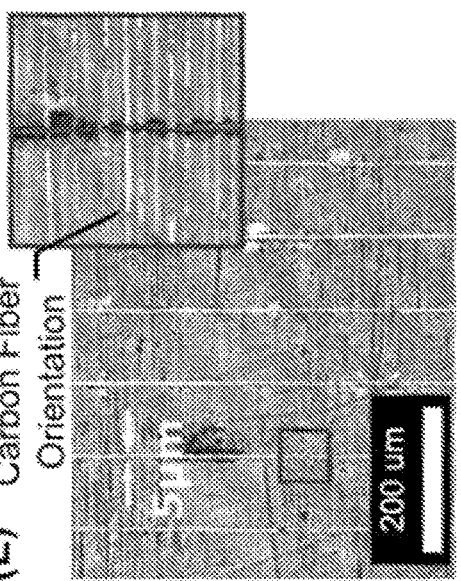
FIG. 3E shows images from an optical microscope of the underside of CFC meander showing trace spacings less than 5 μm and carbon the fiber orientation (lateral).

Referring first to FIG. 2A, section (iii), an electrically conductive member 110 (here a micro-scale meander) may be laser-machined out of an anisotropically conductive material, such as the CFC material shown in FIG. 3D and FIG. 3E. In this work we fixed the separation distance between elements 112 to be the maximum resolution of our laser system, being less than 10 μm typically. The local variation in gap width was high due to the roughness of the edge of each element 112 produced by our machining process (see FIG. 3D, inset). However this variability could be reduced in future by further optimization of the machining parameters. Microscopy analysis of the prototype sensor 100 revealed that adjacent elements 112, in some cases, did not make conformal contact along the entire length of the contact area 114. However, the net contact area 114 from sensor to sensor was sufficiently constant, resulting in relatively repeatable sensor performance. The in-plane thickness dimension of conducting member 110 was about 70 μm and was also limited by the maximum resolution of our laser system. In various embodiments, the thickness dimension of elements 112 and/or the separation distance between elements may be less than 70 μm and 10 μm, respectively. For example, we believe that in-plane thickness dimensions of about 30 μm are achievable with current technology.

Referring back to FIG. 2A, sections (i), (ii), encapsulation 120 (or here, layer 122 thereof) may be prestretched uniaxially (or biaxially) in preparation for receiving conductive member 110. Referring to section (iv), electrically conductive element 110 may then be adhered to the prestretched layer 122 using an pressure sensitive adhesive (PSA). Referring to section (v), second layer 124, which in an embodiment may be the same thickness as layer 122, may then be prestretched and placed on top of electrically conductive member 110 so as to encapsulate electrically conductive member 110 between layer 122 and layer 124. Referring to section (vi), the prestretch in encapsulation 120 (e.g., in layers 122, 124) may be subsequently released and the elastic energy stored in the encapsulation 120 is transmitted to elements 112 of electrically conductive member 110 through the PSA. With sufficient prestretch, adjacent elements 112 can be made to come in to electrical contact, creating a parallel conduction path (with a reduced path length) via the contacted portions 114, hence reducing the overall resistance of sensor 100. FIG. 2B illustrates the aforementioned process with corresponding section labels (i.e., labels (i)-(vi)) for further clarity. Additionally or alternatively, in an embodiment, a heat-bondable material, such as thermoplastic polyurethane (TPU) may be coated onto the surfaces of conductive member 110 during fabrication and subsequently heat bonded to encapsulation 120 without the use of a PSA. In an embodiment, first layer 122 may be stretched by up to 5% more or less than second layer 124.

FIG. 2D is an example of a sensor response from a fabricated device.

Function and Advantages

Applying a strain to sensor 100 may change the amount of stress transmitted to elements 112, and therefore the contact portion 114 between adjacent elements 112. Here we use a laser system able to produce repeatable spacings between adjacent elements 112 of less than 10 μm, which allows sensor 100 to be sensitive over small strains.

Using this mechanism we have been able to demonstrate large changes in electrical resistances of more than two orders of magnitude, from applied strains of less than 3%, opening the door to a new class of highly sensitive strain gauges and strain sensors. Moreover, gauge factors (defined as the change in electrical resistance divided by the initial resistance multiplied by the mechanical sensors $\Delta R/(R_0\varepsilon)$ as large as 5000 in a range 0-2% strain have been demonstrated to date. Stated otherwise, strain sensor 100, in an embodiment, may be capable of transducing strains of less than about 3% as changes in electrical resistance on the scale of 50,000 ohms.

The mechanism represents a paradigm shift compared to most strain sensing methodologies which typically rely upon changes in length or cross-sectional geometry of conductive traces to bring about changes in electrical resistance. In this work, we utilize changes in electrical contact between conductive elements 112 to change the effective path length (without changing the actual length of electrically conductive member 110) by short-circuiting electrically conductive member 110 at several locations, thereby changing its overall resistance. In this respect, sensor 100 can be thought of as a planar, compliant, strain-mediated variable resistor, in that the resistance of the conductor does not change appreciably, just the resistance path length.

Our sensor design has several advantages over conventional strain gauge/force sensor technologies, such as those using sputtered metals on stiff polymeric substrates:

- In this work, we use flexible and mechanically robust electrical conductors (such as carbon fiber composites (CFC)) as the anisotropic conductor, providing a large degree of mechanical flexibility, robustness and therefor ability to sustain several bending cycles and improve overall damage resilience.
- The design of strain sensor 100 allows some embodiments to be about ten times as sensitive to tension as bending.
- The resulting sensors can exhibit extremely large gauge factors, defined as the change in electrical resistance dived by the product of the initial resistance and the mechanical strain ($\Delta R/(R_0\varepsilon)$). We demonstrate gauge factors as large as 5,000 to date.
- Compared to other highly sensitive strain sensors, such as those developed by Kang et al. [9] and Zhou et al. [10], the macroscopic geometry is prescribed by design, allowing greater control over the strain response.
- In comparison to their tradition strain gage counterparts, these gauges are more compliant and conformal due to the use of elastomer substrates and CFC conductors rather than rigid polymers. Additionally, elastomers which can be heat bonded to textiles can be used, making the sensor amenable to textile integration for wearable applications or soft robotic applications.
- The periodic structure of meander and the mechanics of encapsulating elastomer combine to produce sensors with good linearity.
- The high sensitivity brings an advantage in terms of reduced complexity for readout electronics. No significant signal amplification or filtering is necessary, in comparison to traditional rigid load cells.

Figure 4A:
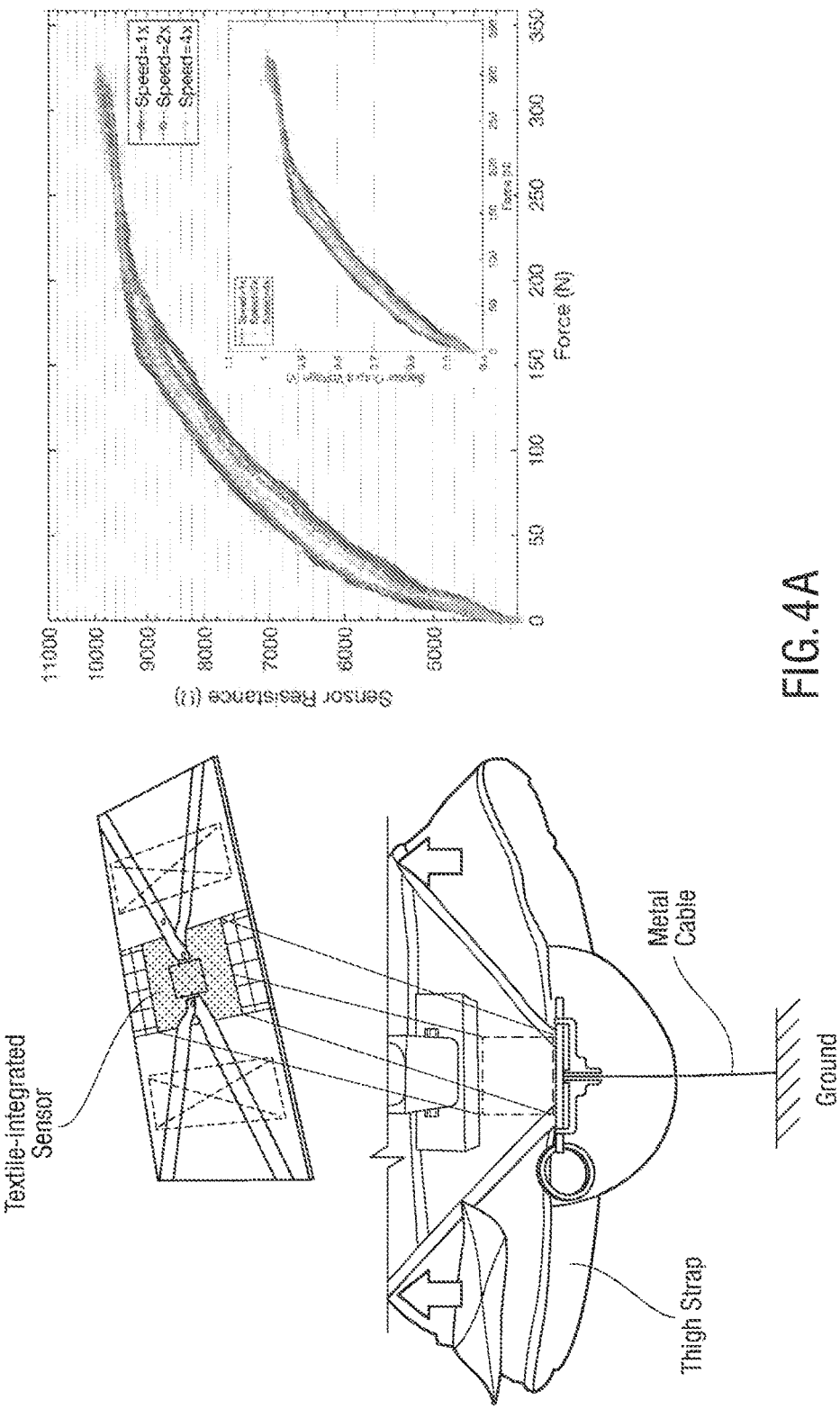
FIG. 4A shows images of a fabricated force sensor bonded to a textile, said sensor integrated into the thigh strap of a soft robotic exosuit system, and a graph depicting said sensor reading as a function of load applied to thigh strap. 300 N is a relevant range for forces applied to this exosuit component during use.

Referring now to FIG. 4A, the efficacy our sensing technology is demonstrated in the integration of the sensor into stiff textiles, showing the ability to integrate this technology into garments and introducing the prospect of a new type of compliant load cell integrated into textiles. Our strain gauge sensor is integrated into the thigh strap of a soft exosuit system [11] being developed at the Wyss at the Harvard Biodesign Laboratory. The thigh strap with integrated sensor is tested using an Instron mechanical tester, which measures the applied forces simultaneously. The change in resistance as a function of tensile force is shown in FIG. 3 for a variety of loading rates. The results show that the sensor is able to detect loads of up to 300 N, which is the typical range of forces experience by this component during operation. The output voltage from our measurement electronics (which consists simply of a current regulator and a 10 V power supply) shows a change in electrical resistance of over half a volt, which is large compared to typical traditional load cells or strain gauges. The sensor response also remains relatively constant over various loading speeds.

Figure 4B:
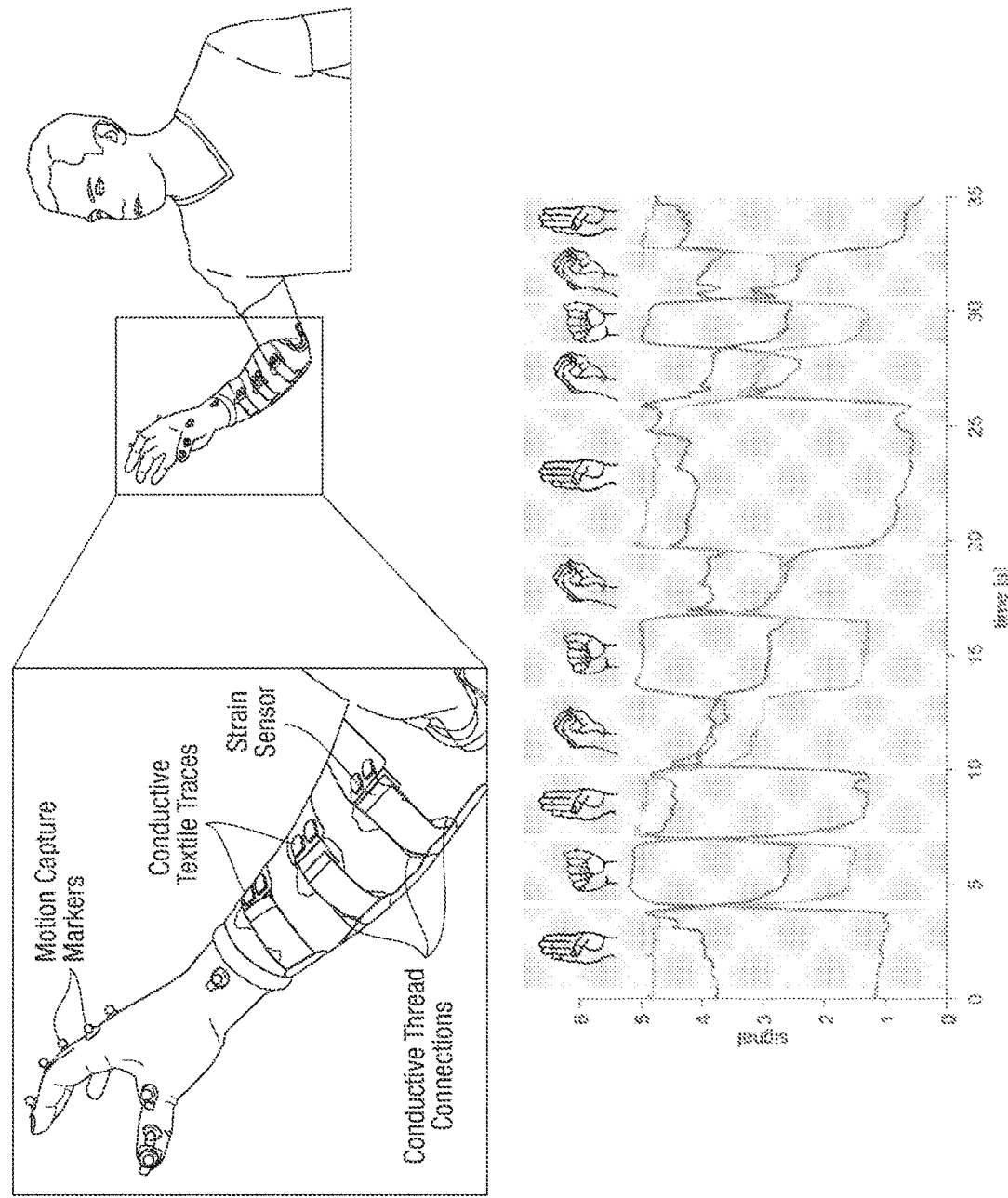
FIG. 4B shows (top) a wearable sensor sleeve with textile integrated sensors attached. The sensors in the sleeve detects subtle deformations on the surface of the forearm which occur in response to hand gestures, and (bottom) corresponding data from the sensors during a gesture sequence used to predict gestures from textile-integrated strain sensors.

Referring now to FIG. 4B, to demonstrate the high sensitivity of the sensing technology, we integrated three sensors into an arm sleeve device and collected data on gesture recognition tasks in a motion capture laboratory (MCL). This data consists of ground truth finger positions from the motion capture cameras, an RGB video stream of all experiments, and the sensor signals from the sleeve-integrated sensors. During these trials, the subject varied their hand gesture between three predefined gestures: an open hand (gesture 0), a closed first (gesture 2), and touching finger tips with extended finger joints (gesture 1). The ground truth MCL data contains the absolute positions of the MCL markers and the relative finger, wrist, and elbow joint angles. We trained a fully connected neural network with two hidden layers (ten nodes each, softmax activation) to predict hand gestures from the data obtained with the sensorized sleeve. The test trial consisted of a series of prescribed gesture transitions; these are shown in FIG. 4B (Bottom), together with the corresponding raw sensor data. It can be seen that the sensor outputs are consistent and reasonably repeatable for a given gesture.

Multi-Axis Force Sensor 200

Here we present a compliant, multi-axis sensor 200 able to detect forces tangential and normal to the sensor surface. In various embodiments, the transduction mechanism is the same or similar to that of sensors 100 above. For example, in various embodiments, multi-axis sensor 200 may measure strain based on the deformation of structures similar to electrically conductive member 110, encapsulated within materials similar to encapsulation 120. Strains in the elastomer material may be transmitted to the electrically conductive members, causing changes in the electrical resistance of the sensor contact mechanics. As such, various embodiments of multi-axis sensor 200 may include similar components as those of sensors 100. Further, multi-axis sensor 200 may include an array of sensors ("sensing array"), and in some embodiments, each such sensor may be similar to or even the same as sensor 100 above. Accordingly, in such cases, any description associated with sensor 100 or components thereof above is hereby incorporated to describe corresponding components of multi-axis sensor 200, unless otherwise specified.

Figures 5A, 5B, 5C:
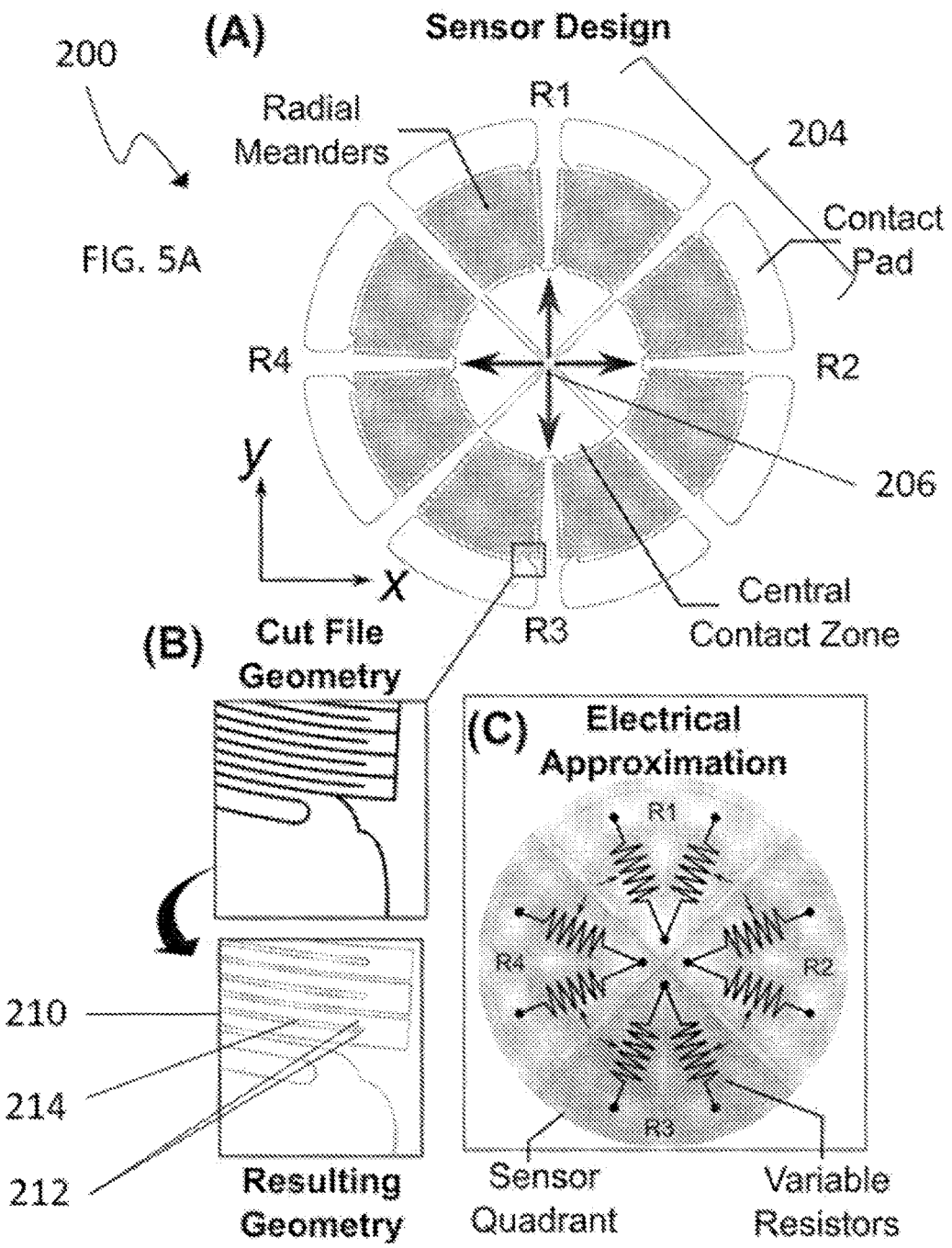
FIG. 5A shows transducer geometry.
FIG. 5B shows a close-up of laser cut file geometry and schematic of resulting transducer geometry.
FIG. 5C shows transducer electrical approximation.

FIG. 5A, FIG. 5B, FIG. 5C, and FIG. 5D illustrate a representative embodiment of multi-axis force sensor 200. Multi-axis force sensor 200, in various embodiments, may generally comprise an array 202 of at least two planar sensors 204, a substrate 230, and a compressible member 240. Generally speaking, at least two planar sensors 204 may be arranged radially about a central portion 206 in antagonistic pairs, and compressible member 240 may be positioned between a substrate 230 and central portion 206 of sensing array 202 so as to displace central portion 206 from substrate 230. Each planar sensor 204 may have similar components and constructions as sensor 100, here with electrically conductive member 210 extending radially as best shown in FIG. 5B and FIG. 8E. By configuring sensors 204 in a radial array, arranging them in antagonistic pairs (here, shown as four quadrants), orienting electrically conductive members 210 to extend radially, and biasing the central portion 206 of the sensing array 202 out-of-plane, multi-axis sensor 200 may detect both tangential and normal forces on multi-axis sensor 200.

Sensing Array 210

As described above, sensing array 202 may include at least two planar sensors 204 arranged radially about a central portion 206 in antagonistic pairs. Each planar sensor 204 may generally include an electrically conductive member 210 and an electrically non-conductive and an elastically deformable material 220 (hereinafter "encapsulation 220"), components similar to electrically conductive member 110 and encapsulation 120 of sensor 100.

Figures 6A, 6B:
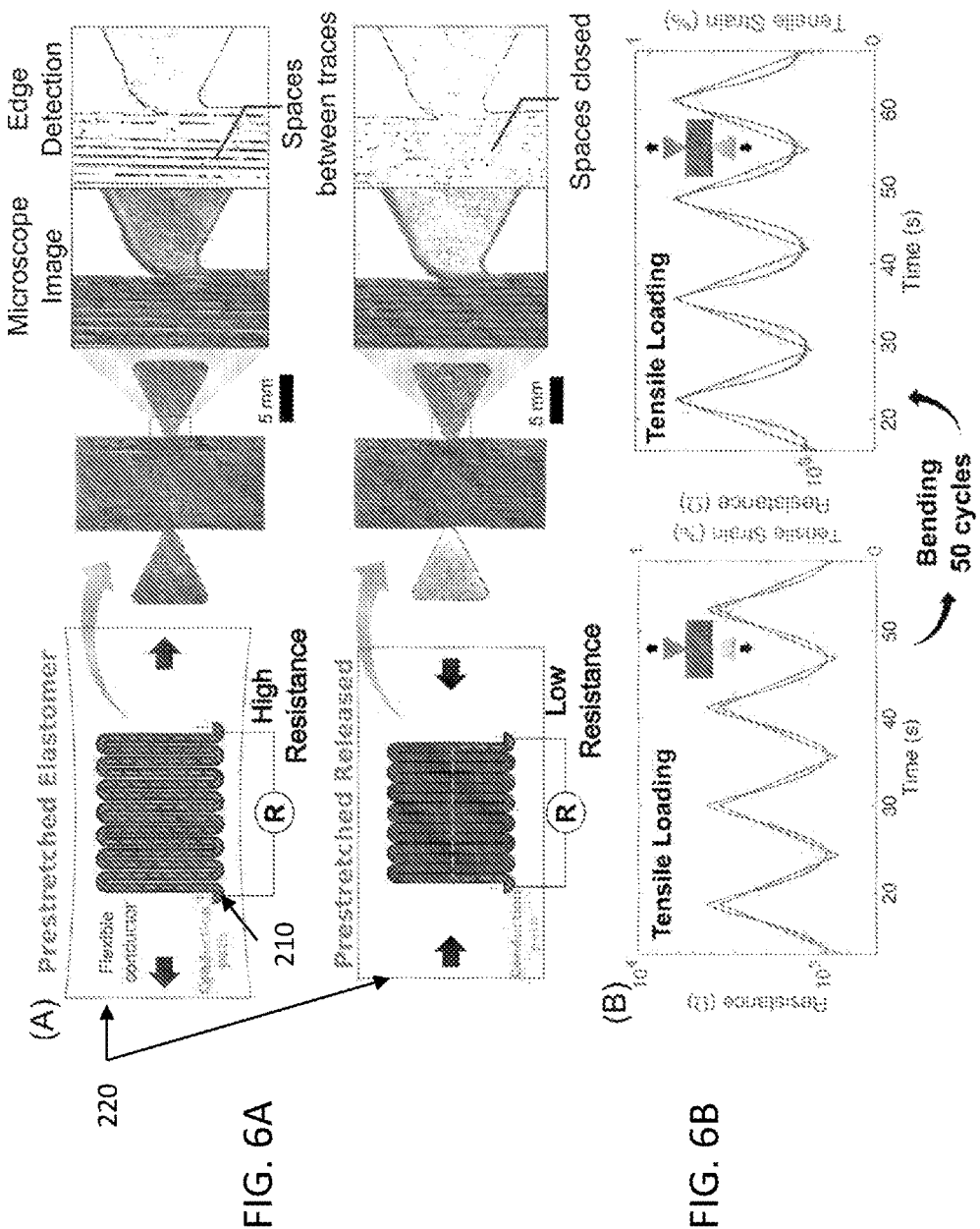
FIG. 6A shows flexible conductors in the shape of a meander, adhered onto a prestretched elastomer substrate. Stretching of the elastomer film changes the electrical conduction path and also the contact area between meander traces (via contact pressure). This changes the overall electrical resistance at the terminal points.
FIG. 6B shows graphs depicting an example of the response of transducer to tensile strain cycles. Qualitative behavior continues even after being subjected to 50 bending cycles.

The sensor working principle is outlined in FIG. 6A. In the embodiment shown, electrically conductive member 210 may be machined into the shape of a meander and bonded to encapsulation 220, here a prestretched elastomer. Prestretching elastomer films generate compressive stresses in the material. If a stiff but flexible material is bonded on top of the elastomer, the elastomer material may buckle out-of-plane when the prestretched is released, and eventually reach an equilibrium state—dependent upon the stored mechanical energy from prestretching, and the energy required to cause bending in the flexible material. However, if the flexible material is micro-structured such that it has a meander shape, and the space between traces is sufficiently small, releasing the prestretch will cause the meanders to buckle in-plane before bending out-of-plane. When the prestretch in the elastomer is released, the underlying elastomer compresses the meanders in-plane, causing the elements 212 (here, strands) to come into contact, short-circuiting the conduction path and substantially reducing the resistance of planar sensor 204. The result is a transduction mechanism with good linearity and an extremely large resistance change, as demonstrated in FIG. 6B. If the flexible material is conductive, the conduction path through the structure may be different between the prestretched and equilibrium states—being high in the prestretched state and low in the equilibrium state. Furthermore, the amount of prestretch governs the contact area between touching traces, mediating the resistance between each trace like a deformation-dependent variable resistor. Hence, deforming the elastomer between the equilibrium and the prestretched states causes a change in resistance which is continuous as shown in FIG. 6B.

In the embodiment shown, meanders are patterned radial rather than linearly, as shown in FIGS. 5B and 8E. Measurements of forces tangential to a surface of sensor 200 (i.e. shear) can be useful for establishing the relative motion between a wearable device or a robotic prosthetic, and the skin of a user, and could help to determine pressure points or areas of excessive friction. As with electrically conducting member 110 of sensor 200, in a representative embodiment, electrically conducting member 210 may be formed of a carbon fiber composite (CFC) material for its combination of good electrical conductivity (electrical sheet resistance measured to be approximately 8 W/sq.) and mechanical flexibility, enabling each planar sensor 204 to be able to withstand bending. Furthermore, the electrical resistance does not change substantially with applied load (for the low loads used in this work) due to its high stiffness. Encapsulation 220, in a representative embodiment, may be formed from thermoplastic polyurethane (TPU) due to its convenience in fabrication, being able to be heat sealed to other TPU layers within seconds, facilitating rapid fabrication.

Substrate 230 and Compressible Member 240

Substrate 230, in various embodiments, may be a rigid, flexible or highly compliant material as the application may determine.

Figure 5D:
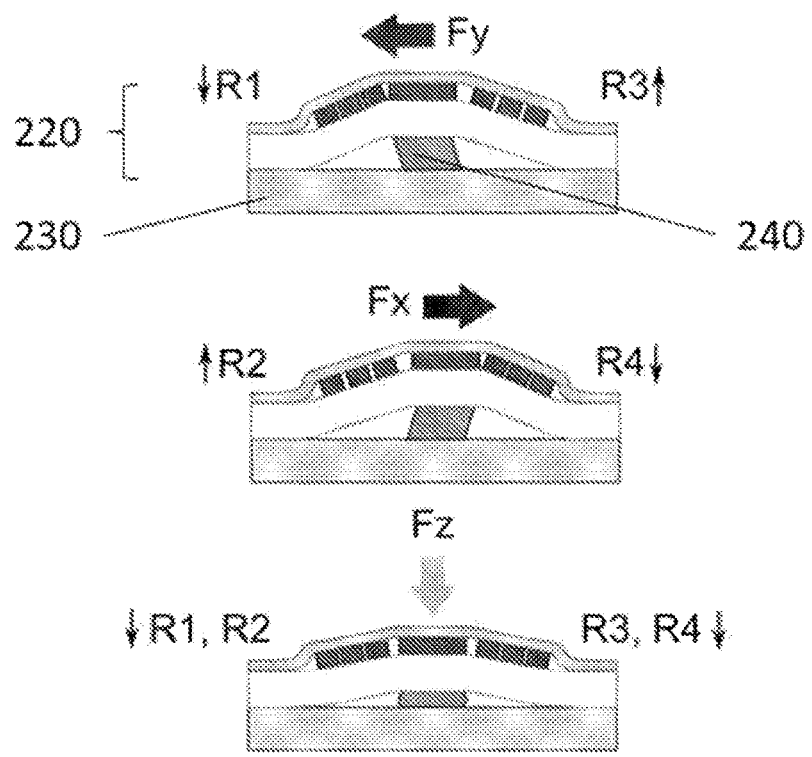
FIG. 5D shows schematic representations of the change in electrical resistance of the sensor in response to various loading conditions.

Compressible member 240, in various embodiments, may be dimensioned and made from any compressible material suitable for displacing central portion 206 of sensing array 202 away from substrate 230. As described above, by biasing central portion 206 out of plane, the sensing array can detect both tangential and normal forces as shown in FIG. 5D. In a representative embodiment, compressible member 240 may be made of foam, which enables the sensor to be sheared more easily, while allowing for a high degree of mechanical compliance. A compressible member 240 made from a less compliant material, such as PDMS (polydimethylsiloxane), can also be used. However, this would make the sensor stiffer and reduce sensor sensitivity.

Design Considerations

We exploit this fundamental transduction principle to develop a sensor 200 capable of sensing forces in multiple axes. The representative design is shown in FIG. 5A, FIG. 5B, FIG. 5C, and FIG. 5D has meanders which are orientated radially, rather than linearly. As shown in FIG. 5A, the illustrated sensor design has four quadrants (two antagonistic pairs of planar sensors 204), which electrically can be thought of as four independent variable resistors as shown in FIG. 5C, where the resistance is based on the change of stretch in each quadrant, as explained above. With the aid of compressible member 240, sensing array 202 may be displaced out-of-plane, which induces a prestretch in the sensor quadrants and offsets the central contact zone 206 from substrate 230.

Referring to FIG. 5D, shear forces (forces applied tangentially to the central region 206 of the sensing array 202) may be detected as a change in length of one resistor quadrant relative to the opposing quadrant. For the application of normal pressure, all four sensor quadrants experience a decrease in length, and therefore a decrease in thickness.

Several parameters may govern the value of resistance between the two states, the most pertinent are listed below:

Elastomer mechanical properties: The stiffness of the elastomer film—a function of the elastic modulus and the film geometry—governs the amount of compressive stresses generated in the film for a given prestretch.

Elastomer prestretch: For a given elastomer film geometry, prestretch governs the amount of compressive stresses generated in the film. Prestretch also has an impact on the linearity of the sensor, depending on if the prestretch exceeds the linear elastic range of the elastomer.

Meander geometry: Governs how easily the meanders can be made to come in contact with each other (i.e. how easily the can be bent in-plane) via the spacing distance, and also sets the limits on the maximum and minimum electrical resistance. This also plays a large role in determining the mechanical compliance of the sensor.

Flexible conductor electrical properties: Sets the limits on the maximum and minimum electrical resistance, for a given meander geometry.

Flexible conductor mechanical properties: Dictates the ease with which the meander traces can be made to touch each other, for a given meander geometry and elastomer stiffness. This also plays a large role in determining the mechanical compliance of the sensor and the mechanical resilience.

Fabrication

FIG. 7A, FIG. 7B, FIG. 7C, FIG. 7D, FIG. 7E, FIG. 7F, FIG. 7G, and FIG. 7H illustrate a representative fabrication methodology for fabricating multi-axis force sensor 200. The methodology exhibited high mechanical compliance with a very low form factor, and enables the reliable and repeatable fabrication of sensors.

Referring first to FIG. 7A, in preparation for making electrically conductive member 210, a CFC lay-up may be made by stacking three layers of carbon fiber sheets pre-impregnated with an epoxy resin (e.g., Toho Tenax, by Teijin), and sandwiching with two layers of 30 µm thick TPU. The three CFC layers are laid orthogonal to each other, as depicted in FIG. 7A. This orthogonal stacking helps to maintain the flatness of the composite by minimizing thermally induced buckling, as well as providing anisotropic properties as discussed in the context of electrically conductive member 110 of sensor 100. The carbon fiber composite lay-up may then be placed in a heat press and may be cured using the manufacture's recommended pressure and heat profiles.

Referring now to FIG. 7B, following the CFC fabrication, encapsulation material 220 may be stretched biaxially in-plane. In the prototype, a 300 µm thick TPU film was stretched approximately 20% biaxially in-plane using a purpose built prestretcher mechanism. As shown in FIG. 7C, the CFC lay-up may then be cut to the desired size, backed on one side with a 5 µm thin double-sided adhesive (82600, by 3M), and adhered to the surface of the prestretched TPU. Referring to FIG. 7D, the geometry of electrically conductive member 210 (here, a meander) may then be laser-machined into the CFC layup using a diode-pumped solid-state laser (e.g., one provided by Oxford Lasers). The spaces between the meander traces (elements 212) are represented by a single cut line in the cut file geometry as shown in FIG. 5B. This minimizes the spacing between the meander traces, hence reducing the amount prestretch required to make the traces come into contact with each other. This also means that the minimum distance between meander traces is determined by the laser beam width. After the laser-machining process is complete, the excess material is removed from TPU film as shown in FIG. 7E.

Referring to FIG. 7F, the prestretch in the TPU film may then be released by carefully removing it from the prestretch mechanism. A second 30 µm thin TPU film may then be placed on top of the CFC and heat-pressed onto the lay-up and underlying TPU film, as shown in FIG. 7G. This serves to encapsulate the CFC traces, fixing the traces in place and protecting them from external disturbances. This also ensures that there is no slip between the TPU layer and the CFC traces. Slip between the TPU and traces would result in a loss of in-plane compressive stress and reduce the sensor repeatability over time.

Referring to FIG. 7H, compressible member 240, shown here as a foam disk approximately 2 mm thick, may then be placed under sensing array 202 at its center, and the perimeter of the sensor array 202 bonded to a PET substrate 230 using a double-sided adhesive (FIG. 3(H)). The foam disk is compressed when sensing array 202 is bonded to the PET substrate, reducing the thickness. The foam thickness was selected as the result of a pre-characterization of different foam thicknesses, and was shown to provide good biasing while not excessively increasing the sensor overall thickness.

Experimental Characterization

FIG. 8A, FIG. 8B, FIG. 8C, FIG. 8D, FIG. 8E, FIG. 8F, FIG. 8G, FIG. 8H and FIG. 8I illustrate a prototype multi-axis sensor 200 and the fabrication process used to make it. The total diameter of the prototype sensor 200 shown in FIG. 8A, FIG. 8B, FIG. 8C, FIG. 8D, FIG. 8E, FIG. 8F, FIG. 8G, FIG. 8H and FIG. 8I is 20 mm, the excess TPU surrounding the sensor 200 is left in place to help with device handling and electrical connections. The sensor 200 demonstrates a high degree of mechanical compliance and conformability. The thickness of the meanders is approximately 70 µm and spaces between meanders approximately 30 µm. The prototype was experimentally characterized and demonstrated large differential changes in resistance (up to 26 kΩ for tangential forces applied to the sensor surface).

Figure 8A:
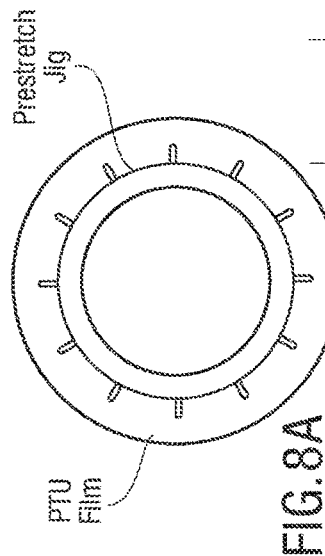
FIG. 8A shows the TPU film and prestretching mechanism placed underneath (made from transparent plexiglass).
Figure 8B:
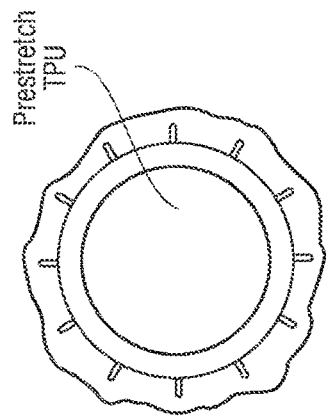
FIG. 8B shows the stretched TPU film.
Figure 8C:
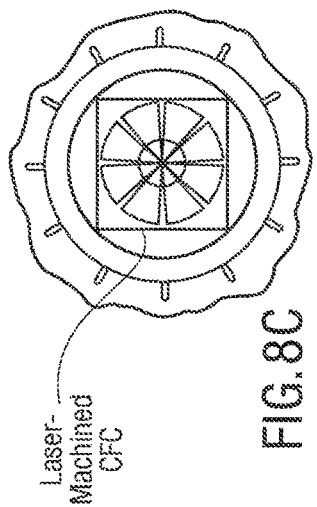
FIG. 8C shows the laser-machined CFC adhered to the stretched TPU.
Figure 8D:
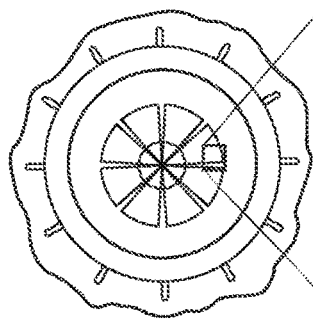
FIG. 8D shows excess CFC material being removed post laser machining.
Figure 8E:
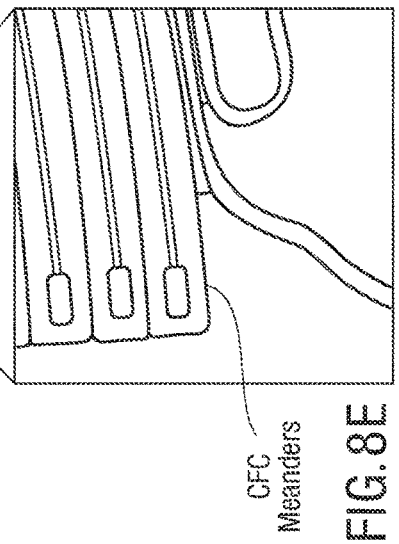
FIG. 8E shows a magnified view of the meander geometry.
Figure 8F:
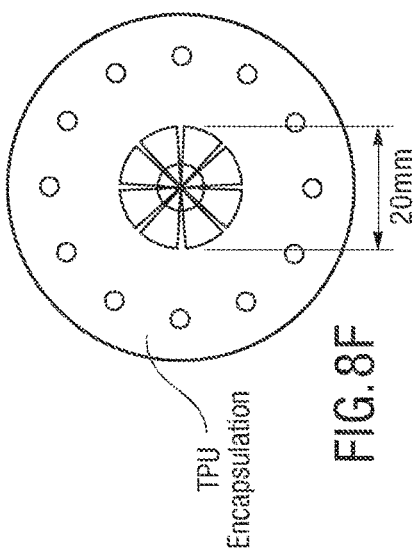
FIG. 8F shows the encapsulated sensor device.

With respect to the fabrication process, FIG. 8A shows the TPU film and prestretching mechanism placed underneath (made from transparent plexiglass). The stretched TPU film is shown in FIG. 8B. Laser-machined CFC is adhered to the stretch TPU film as shown in FIG. 8C. Excess CFC material is removed after the laser machining process as shown in FIG. 8D. The meander geometry can be seen in FIG. 8E and is shaded for clarity. Encapsulation is applied and the resulting encapsulated sensor is shown in FIG. 8F. In FIG. 8G, a foam disk is adhered to the sensor underside and in FIG. 8H electrical connections are made using metal pins inserted through CFC and TPU layers. FIG. 8I illustrates the sensor being bent, demonstrating the sensor's compliance and low form factor.

Figures 9A, 9B:
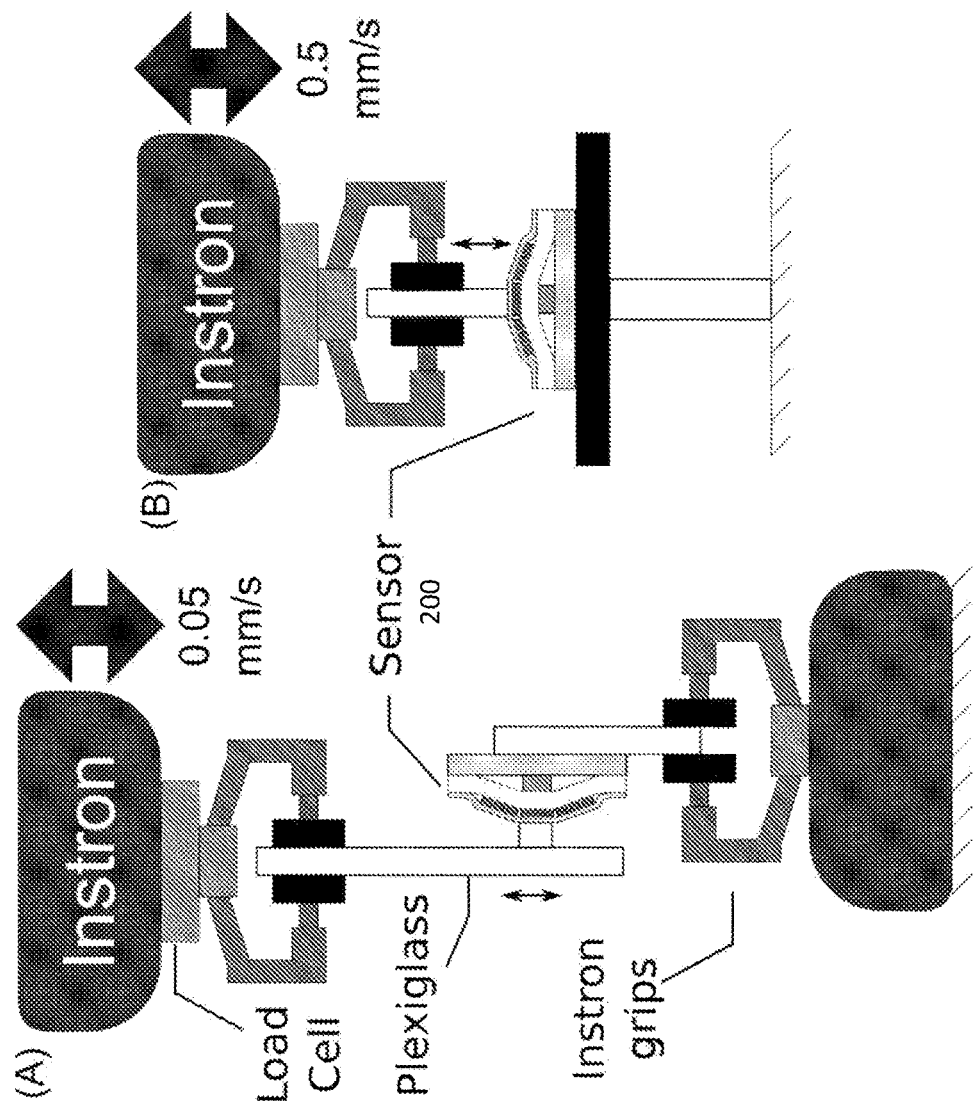
FIG. 9A shows a test configuration for characterizing forces in x and y.
FIG. 9B shows a test configuration for measuring normal forces.

We characterize the prototype multi-axis force sensor 200 using the experimental set-up schematically depicted in FIG. 9A and FIG. 9B. A probe made of plexiglass (or acrylic) is attached to the center of the multi-axis force sensor 200 at one end, and to the moving head of an Instron mechanical tester (model 5544A) at the other. For ease of characterization, electrical connections are facilitated via metal pins which puncture through the sensor contact pads as shown in FIG. 8H, making a through-hole connection. The resistance of the each of the sensor quadrants is measured using a four-point measurement technique in order to mitigate the effect of contact resistance.

Data acquisition was performed using a National Instruments DAQ board and synchronized with the mechanical data via the Instron software interface (sample rate was 10 ms). Forces were applied tangentially to the sensor surface in both in-plane dimensions with a magnitude of ±1 N at a speed of 0.05 mm/s for three cycles. A normal force was also applied to the sensor in the range −8 N and 0 N at a speed of 0.5 mm/s for three cycles (the force and speed settings were increased for the normal force tests due to the increased range of motion in the sensor in the normal direction).

Figure 10A:
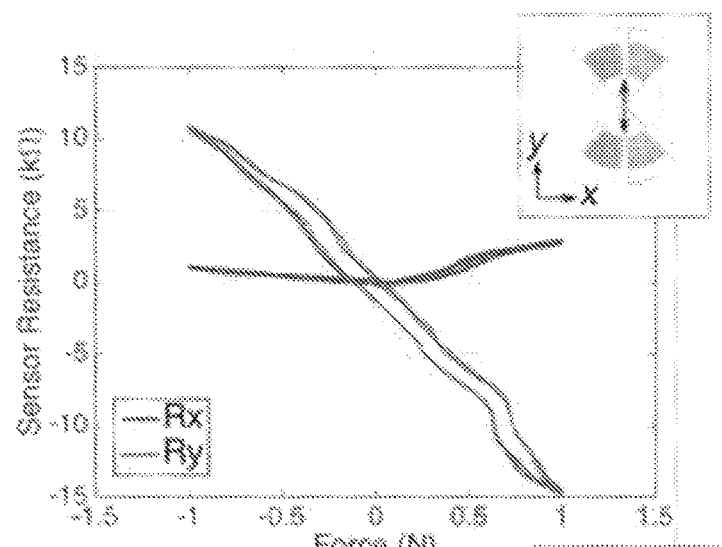
FIG. 10A shows a graph of the results for applied forces in x-dimension.
Figure 10B:
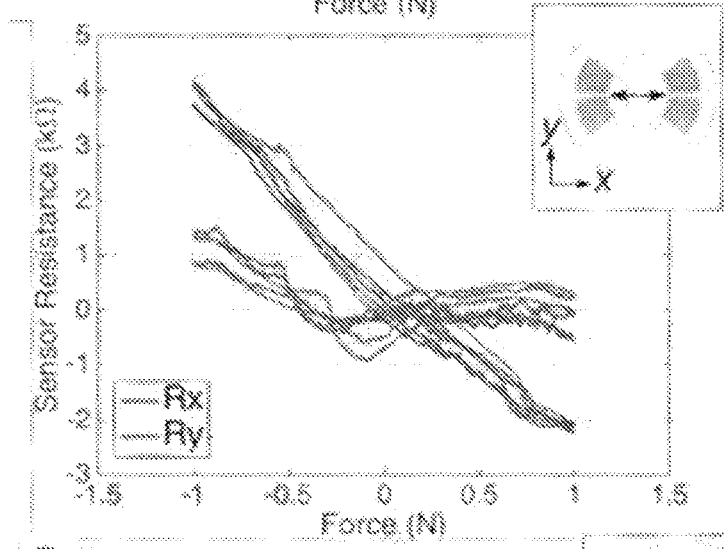
FIG. 10B shows a graph of the results for applied forces in y-dimension.
Figure 10C:
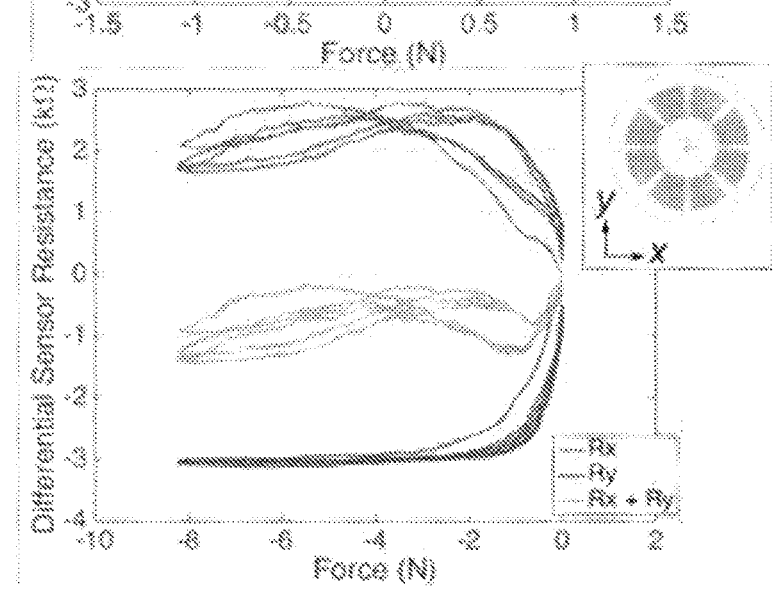
FIG. 10C shows a graph of the results for applied forces in z-dimension.

FIG. 10A, FIG. 10B, and FIG. 10C show the results of the sensor characterization. The results are presented as the difference in the resistance of antagonist sensor quadrants, and subtracted by the initial differential value i.e. $Rx=(R_1-R_3)-(_1{}^0-R_3{}^0)$ and $Ry=(R_2-R_3)-(R_2{}^0-R_4{}^0)$, where subscript numbers 1, 2, 3 and 4 correspond to the four sensor quadrants, the superscript 0 denotes the value at time=0 i.e. at the start of the experiment, and Rx is the and Ry are the differential resistances plotted in the figures. As can be seen from the figures, a substantial differential resistance was measured for the shear measurements. A differential resistance $Rx>25$ k$\Omega$ was seen for shear in the x-direction over the applied force range (FIG. 6(A)). This is approximately 10 times greater than the variation seen in the orthogonal antagonist quadrant pair Ry. Moreover, both the sensor linearity (R2 value of 0.9829) of and repeatability over the three cycles are acceptable for many robotic sensing applications.

A lower differential resistance Ry can be seen for shear in the y-direction (approximately 6 k$\Omega$) as seen in FIG. 10B. This may be due in part to the anisotropy in electrical anisotropy, which is oriented to be higher in the y dimension (following the convention shown in the inset of FIG. 10A, FIG. 10B, and FIG. 10C). Another contributing factor, is manufacturing error and the difficulty in placing the plexi-glass (or acrylic) probe perfectly in the center of the device. Despite this, the linearity in the sensor signal remains ($R^2$ value of 0.9629). The response of the multi-axis force sensor 200 to normal pressure is shown in FIG. 10C. The differential resistances Rx and Ry approximately mirror each other about the zero value. At lower values of compressive force, below 2 N, there is a relatively steep change in the differential resistances (between 2-3 N). For compressive forces greater than 2 N, the differential resistances saturate. This can be explained through the compression of the foam core, which ceases to act as a biasing mechanism for the sensor, and thus the associated prestretch in the device is released.

Figure 11A:
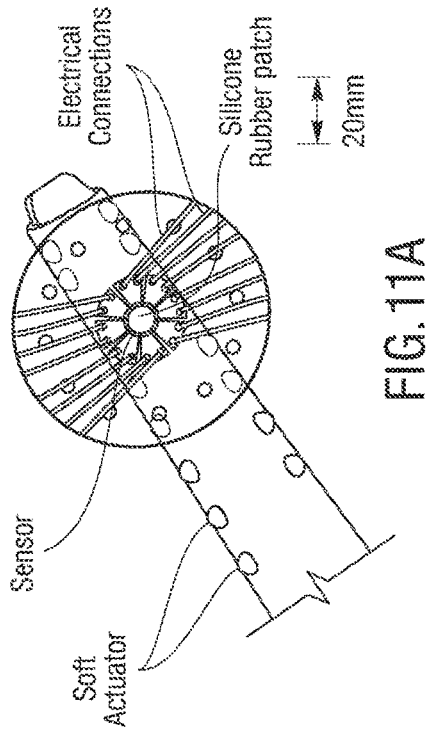
FIG. 11A shows an integration of the compliant sensor onto a soft actuator finger from a soft robotic gripper.
Figure 11B:
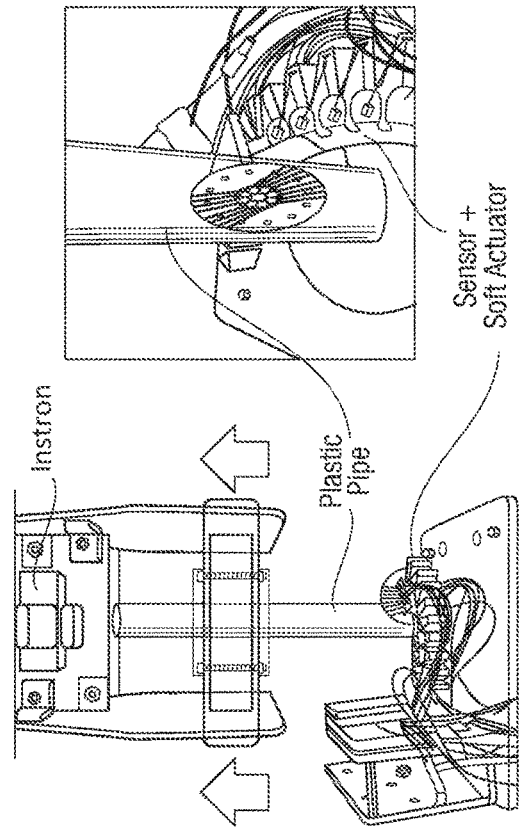
FIG. 11B shows an experimental set-up for a friction detection demonstration.
Figure 11C:
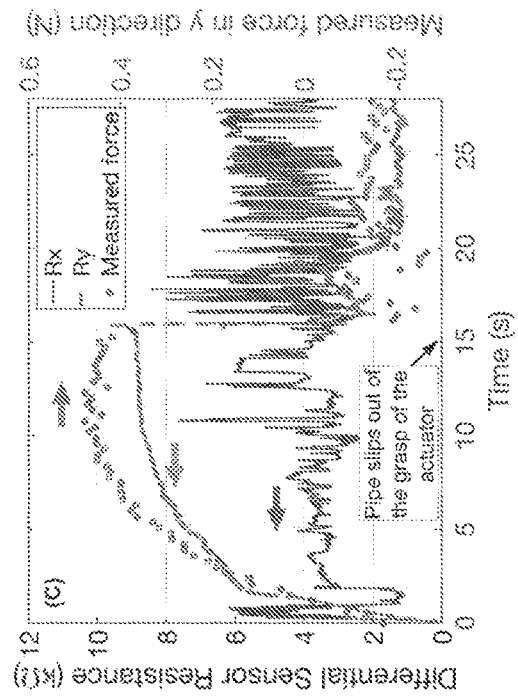
FIG. 11C shows a graph of the results of the friction detection demonstration.

Referring now to FIG. 11A, FIG. 11B, and FIG. 11C, we integrate our sensor technology onto the finger actuator of the soft robotic gripper developed Galloway et al. [12] in order to demonstrate the ability to detect contact forces in real-world robotic systems. Sensor integration was performed by heat-pressing a sensor onto a TPU coated textile, and threading the textile onto purpose made holes cast into the soft actuator structure. The result of the sensor integration is show in FIG. 11A, FIG. 11B, and FIG. 11C (the TPU material surrounding the sensor was kept in place as it proved convenient for making electrical connections). A circular PDMS film was attached to the central contact zone of the sensor to increase friction. A 1 inch diameter plastic pipe was attached to an Instron mechanical tester and was placed in the path of the actuator, and the actuator subsequently pressurized to 20 psi, causing it to curl around the pipe as shown in FIG. 11B. The plastic pipe was then displaced vertically at a rate of 1 mm/s until a point at which is lost contact with the surface of the actuator (occurring at approximately 16 seconds). The sensor resistance was measured simultaneously using the set-up mentioned above. The results of this experiment are shown in FIG. 11C. A clear difference can be seen between the differential resistance values, Rx and Ry. Ry represents the output from the antagonistic quadrant pair parallel to the direction of travel of the plastic pipe (note, $R_z$ is not shown as this requires the development of decoupling relationship, which is beyond the scope of this preliminary investigation). The value of Ry increases gradually until it begins to plateau at around 11 seconds (indicated by the plateau in the Instron force reading). This period represents a phase where the sensor is deformed through contact with the moving pipe until it reaches a stable position and starts to slip. At 16 seconds the pipe slips completely from the out of the grasp of the soft actuator (as indicated by the reduction in force measured by the Instron load cell), at which point the value for Ry returns to near the baseline value. The value Rx is relatively more noisy, potentially due to excessive deformation of the sensor connections as the actuator is deformed by the pipe.

Discussion and Conclusion

The multi-axis force sensor 200 developed in this work was fabricated using a custom manufacturing methodology and exhibits a high degree of mechanical compliance. The fabricated multi-axis force sensor 200 has demonstrated the ability to detect forces applied tangentially and normally to the sensor surface. Moreover the sensor signal is reasonably linear and repeatable. The changes in electrical resistance induced by forces are in the thousands of Ohms, and hence can be measured without the use of complex signal conditioning or amplification circuits. The high compliance of the multi-axis force sensor 200 enables it to conform to non-planar surfaces, such as the surface of a soft robotic gripper finger. In various embodiments, the forces applied to multi-axis force sensor 200 could be fully decoupled in all three axis. This would also prove useful for optimizing the sensor fabrication parameters, such as prestretch value and meander geometry, in order to maximize the signal to noise ratio.

The transduction mechanism is based on changes in contact resistance between elements 212 of electrically conductive members 210 bonded to encapsulation material 220. The sensor resistance is mediated by compressive stresses in the encapsulation material 220. In order to measure forces in multiple axes, the electrically conductive members 210 may be oriented radially and segmented into four quadrants (two antagonist pairs) or more, and the central region 206 of sensing array 202 may be offset out-of-plane by a compressible member 240, such as a foam biasing element. Prototype multi-axis force sensors 200 were fabricated using a custom fabrication system and exhibited a high degree of mechanical compliance. The multi-axis force sensors 200 demonstrated the ability to detect and distinguish forces tangential to the sensor surface, as well as normal to the sensor surface. Moreover, resistance changes in the thousands of Ohms were measured for applied tangential forces in the range ±1 N, more than 10 times that recorded for the orthogonal antagonist pair, and in a range which can be easily measured with simple electronic circuits. The multi-axis force sensor 200 was integrated onto the surface of a soft robotic gripper finger and friction force detection was demonstrated, validating the efficacy of our technology in real world systems.

[1] A. Atalay, V. Sanchez, O. Atalay, D. M. Vogt, F. Haufe, R. J. Wood, and C. J. Walsh, "Batch Fabrication of Customizable Silicone-Textile Composite Capacitive Strain Sensors for Human Motion Tracking," Advanced Materials Technologies, vol. 1700136, p. 1700136, 2017.

[2] A. P. Gerratt, H. O. Michaud, and S. P. Lacour, "Elastomeric Electronic Skin for Prosthetic Tactile Sensation," Advanced Functional Materials, vol. 25, no. 15, pp. 2287-2295, 2015.

[3] Y. Menguc, Y.-L. Park, H. Pei, D. Vogt, P. M. Aubin, E. Winchell, L. Fluke, L. Stirling, R. J. Wood, and C. J. Walsh, "Wearable soft sensing suit for human gait measure-

[4] D. P. J. Cotton, I. M. Graz, and S. P. Lacour, "A multifunctional ca-pacitive sensor for stretchable electronic skins," IEEE Sensors Journal, vol. 9, no. 12, pp. 2008-2009, 2009.

[5] B. Nie, R. Li, J. Cao, J. D. Brandt, and T. Pan, "Flexible Transparent Iontronic Film for Interfacial Capacitive Pressure Sensing," Advanced Materials, pp. n/a-n/a, 2015.

[6] J.-Y. Sun, C. Keplinger, G. M. Whitesides, and Z. Suo, "Ionic Skin," Advanced Materials, vol. 26, no. 45, pp. 7608-7614, 2014.

[7] D. M. Vogt, Y.-L. Park, and R. J. Wood, "Design and Characterization of a Soft Multi-Axis Force Sensor Using Embedded Microfluidic Channels," IEEE Sensors Journal, vol. 13, no. 10, pp. 4056-4064, October 2013.

[8] S. Toyama, Y. Tanaka, S. Shirogane, T. Nakamura, T. Umino, R. Uehara, T. Okamoto, and H. Igarashi, "Development of Wearable Sheet-Type Shear Force Sensor and Measurement System that is Insusceptible to Temperature and Pressure," Sensors, vol. 17, no. 8, p. 1752, 2017.

[9] D. Kang, P. V. Pikhitsa, Y. W. Choi, C. Lee, S. S. Shin, L. Piao, B. Park, K.-Y. Suh, T.-i. Kim, and M. Choi, "Ultrasensitive mechanical crack-based sensor inspired by the spider sensory system," Nature, vol. 516, no. 7530, pp. 222-226, 2014.

[10] J. Zhou, H. Yu, X. Xu, F. Han, and G. Lubineau, "Ultrasensitive, Stretchable Strain Sensors Based on Fragmented Carbon Nanotube Papers," ACS Applied Materials and Interfaces, vol. 9, no. 5, pp. 4835-4842, February 2017.

[11] F. Panizzolo, I. Galiana, A. T. Asbeck, C. Siviy, K. Schmidt, K. G. Holt, and C. J. Walsh, "A biologically-inspired multi joint soft exosuit that can reduce the energy cost of loaded walking," Journal of Neuroengineering and Rehabilitation, vol. submitted, no. 1, p. 43, 2016.

[12] K. C. Galloway, K. P. Becker, B. Phillips, J. Kirby, S. Licht, D. Tchernov, R. J. Wood, and D. F. Gruber, "Soft Robotic Grippers for Biological Sampling on Deep Reefs," Soft Robotics, vol. 3, no. 1, pp. 23-33, March 2016.

While the presently disclosed embodiments have been described with reference to certain embodiments thereof, it should be understood by those skilled in the art that various changes may be made and equivalents may be substituted without departing from the true spirit and scope of the presently disclosed embodiments. In addition, many modifications may be made to adapt to a particular situation, indication, material and composition of matter, process step or steps, without departing from the spirit and scope of the present presently disclosed embodiments. All such modifications are intended to be within the scope of the claims appended hereto.

What is claimed is:

1. A strain sensor, comprising:
   an electrically conductive member having a plurality of elements arranged adjacent to one another; and
   an electrically non-conductive and elastically deformable material encapsulating the electrically conductive member,
   wherein, when the sensor is in an equilibrium state, compressive forces stored in the electrically non-conductive and elastically deformable material cause at least one of the plurality of elements to contact at least a portion of an adjacent element of the electrically conductive member, thereby forming an electrically conductive pathway between the adjacent elements through the contacted portion, and
   wherein, when a strain is applied to the sensor, a resulting elastic deformation of the electrically non-conductive and elastically deformable material causes the at least one of the plurality of elements to space apart from the adjacent element such that the contacted portion decreases or is eliminated, thereby reducing or eliminating the electrically conductive pathway between the adjacent elements and increasing a resistance of the electrically conductive member.

2. The strain sensor of claim 1, wherein the electrically non-conductive and elastically deformable material is an elastomer material.

3. The strain sensor of claim 1, wherein the electrically non-conductive and elastically deformable material includes a first layer and a second layer positioned on opposing sides of the electrically conductive member.

4. The strain sensor of claim 1, wherein at least some of the plurality of elements are oriented parallel to one another or within about 30 degrees of being parallel to one another.

5. The strain sensor of claim 1,
   wherein the electrically conductive member is a continuous structure including sections that are arranged to be adjacent to one another, and
   wherein the plurality of elements are defined by the sections of the continuous structure.

6. The strain sensor of claim 5, wherein the electrically conductive member has a meander shape.

7. The strain sensor of claim 1, wherein electrically conductive member is formed of a carbon fiber composite material or a super elastic alloy or shape-memory alloy.

8. The strain sensor of claim 1, wherein at least some of the plurality of elements are arranged substantially parallel to one another.

9. The strain sensor of claim 1, wherein at least some of the plurality of elements of the electrically conductive member have anisotropic conductivity.

10. The strain sensor of claim 1, wherein at least some of the plurality of elements of the electrically conductive member have an in-plane thickness dimension of at least about 30 micrometers.

11. The strain sensor of claim 1, wherein the plurality of elements of the electrically conductive member are spaced apart by about 10 micrometers or less when not under in-plane compression by the electrically non-conductive and elastically deformable material.

12. The strain sensor of claim 1, wherein the strain sensor is substantially planar in shape.

13. The strain sensor of claim 1, wherein the electrically non-conductive and elastically deformable material can be heat bonded to a textile material.

14. The strain sensor of claim 1, wherein the strain sensor is capable of transducing strains of less than about 3% as changes in electrical resistance on the scale of 50,000 ohms.

15. The strain sensor of claim 1, wherein the strain sensor has a gauge factor of up to about 5,000 in a range of about 0% to about 2% strain.

16. The strain sensor of claim 1, wherein the strain sensor is about ten times as sensitive to tension as bending.

17. A multi-axis force sensor, comprising:
   a planar substrate;
   a sensing array comprising at least two planar sensors arranged radially on the substrate in antagonistic pairs, each planar sensor comprising:
      an electrically conductive member extending radially and having a plurality of elements arranged adjacent to one another, and an electrically non-conductive and elastically deformable material encapsulating the electrically conductive member and applying an in-plane compressive force on the electrically conductive member; and a compressible member positioned between the substrate and a central portion of the sensing array, the compressible member acting to displace the central portion of the sensing array away from the substrate.

18. The multi-axis force sensor of claim 17, wherein, in response to a force applied tangentially to the central portion of the sensing array, the plurality of elements of at least one of the planar sensors space apart from one another, thereby reducing a contact area between adjacent elements of the corresponding planar sensor and increasing an electrical resistance of the corresponding planar sensor.

19. The multi-axis force sensor of claim 18, wherein the direction and magnitude of the force applied tangentially to the central portion of the sensing array is correlatable to a relative change in resistance amongst the antagonistically-situated pair or pairs of planar sensors of the sensing array.

20. The multi-axis force sensor of claim 17, wherein, in response to a force applied normal to the central portion of the sensing array, the plurality of elements in each of the at least two planar sensors compress towards one another, thereby increasing a contact area between adjacent elements of the corresponding planar sensor and decreasing an electrical resistance of the corresponding planar sensor.

21. The multi-axis force sensor of claim 20, wherein the magnitude of the force applied normal to the central portion of the sensing array corresponds to a change in resistance of the at least two planar sensors.

22. A method for manufacturing a force sensor, the method comprising:

encapsulating an electrically conductive member within an electrically non-conductive and elastically deformable material, the electrically conductive member comprising a plurality of elements arranged adjacent to one another and spaced apart from one another; and contracting or allowing the electrically non-conductive and elastically deformable material to contract in-plane, thereby causing each of the plurality of elements to contact at least a portion of an adjacent element of the electrically conductive member.

23. The method of claim 22,
wherein the electrically conductive member extends linearly in-plane with the force sensor, and
wherein contracting or allowing the electrically non-conductive and elastically deformable material to contract in-plane is configured to apply uniaxial compressive force on the electrically conductive member.

24. The method of claim 22,
wherein the electrically conductive member extends radially, and
wherein contracting or allowing the electrically non-conductive and elastically deformable material to contract in-plane is configured to apply biaxial compressive force on the electrically conductive member.

25. The method of claim 22, wherein contracting or allowing the electrically non-conductive and elastically deformable material to contract includes:

stretching the electrically non-conductive and elastically deformable material prior to encapsulating the electrically conductive member, and releasing the stretching of the electrically non-conductive and elastically deformable material.

26. The method of claim 25, wherein the electrically non-conductive and elastically deformable material remains stretched by about 5% after being allowed to contract.

27. The method of claim 22,
wherein the electrically non-conductive and elastically deformable material is configured to contract in the presence of heat energy, and
wherein contracting or allowing the electrically non-conductive and elastically deformable material to contract includes heating the electrically non-conductive and elastically deformable material to a temperature at which the material contracts.

28. The method of claim 27, wherein the electrically non-conductive and elastically deformable material includes a first layer and a second layer.

29. The method of claim 28, wherein the first layer is contracted by up to 5% more or less than the second layer.

30. The method of claim 28, wherein the first layer has a different thickness dimension than the second layer.

31. The method of claim 22,
wherein the electrically non-conductive and elastically deformable material includes a first layer and a second layer, and
wherein stretching the electrically non-conductive and elastically deformable material includes stretching the first layer and stretching the second layer, and
wherein encapsulating the electrically conductive member includes situating the electrically conductive member between the first stretched layer and the second stretched layer of the electrically non-conductive and elastically deformable material.

32. The method of claim 31, wherein the first layer is stretched by up to 5% more or less than the second layer.

33. The method of claim 31, wherein the first layer has a different thickness dimension than the second layer.

34. The method of claim 31, wherein the first layer has different mechanical properties than the second layer.

35. The method of claim 22,
wherein the electrically non-conductive and elastically deformable material is an elastomer material;
wherein the of the electrically conductive member is formed of a carbon fiber composite material or a super elastic shape-memory alloy;
wherein the plurality of elements of the electrically conductive member have an in-plane thickness dimension of at least about 30 micrometers;
wherein the plurality of elements of the electrically conductive member are spaced apart from one another by about 10 micrometers.

36. The method of claim 35, wherein the electrically non-conductive and elastically deformable material is contracted or allowed to contract in-plane by about 5%.

37. The method of claim 36, wherein the sensor has a gauge factor of up to about 5,000 in a range of about 0% to about 2% strain.

* * * * *

UNITED STATES PATENT AND TRADEMARK OFFICE
CERTIFICATE OF CORRECTION

PATENT NO. : 11,422,045 B2
APPLICATION NO. : 17/056357
DATED : August 23, 2022
INVENTOR(S) : Oluwaseun A. Araromi et al.

It is certified that error appears in the above-identified patent and that said Letters Patent is hereby corrected as shown below:

In the Claims

In Claim 32, at Column 20, Lines 36, the text: "The method of claim 31" should be replaced with:
-- The method of claim 28 --.

In Claim 33, at Column 20, Lines 38, the text: "The method of claim 31" should be replaced with:
-- The method of claim 28 --.

In Claim 34, at Column 20, Lines 40, the text: "The method of claim 31" should be replaced with:
-- The method of claim 28 --.

Signed and Sealed this
Fifteenth Day of November, 2022

Katherine Kelly Vidal
*Director of the United States Patent and Trademark Office*